US008609068B2

(12) United States Patent
Hagar et al.

(10) Patent No.: US 8,609,068 B2
(45) Date of Patent: Dec. 17, 2013

(54) CONTINUOUS SILICA PRODUCTION PROCESS AND SILICA PRODUCT PREPARED FROM SAME

(75) Inventors: William J. Hagar, Perryville, MD (US); Karl W. Gallis, Perryville, MD (US)

(73) Assignee: J.M. Huber Corporation, Atlanta, GA (US)

( * ) Notice: Subject to any disclaimer, the term of this patent is extended or adjusted under 35 U.S.C. 154(b) by 716 days.

(21) Appl. No.: 12/711,321

(22) Filed: Feb. 24, 2010

(65) Prior Publication Data

US 2011/0206746 A1 Aug. 25, 2011

(51) Int. Cl.
*A61K 9/16* (2006.01)
*A61Q 11/00* (2006.01)
*C01B 33/187* (2006.01)

(52) U.S. Cl.
CPC .............. *A61Q 11/00* (2013.01); *A61K 9/1611* (2013.01); *C01B 33/187* (2013.01); *C01P 2004/30* (2013.01); *C01P 2006/19* (2013.01); *C01P 2004/61* (2013.01); *C01P 2006/21* (2013.01); *C01P 2006/12* (2013.01)
USPC ............. 424/49; 424/401; 424/489; 423/335; 428/402

(58) Field of Classification Search
None
See application file for complete search history.

(56) References Cited

U.S. PATENT DOCUMENTS

| | | | |
|---|---|---|---|
| 3,324,093 A | 6/1967 | Alleman | |
| 3,987,096 A | 10/1976 | Fuchs | 260/566 |
| 4,001,379 A | 1/1977 | Türk et al. | 423/339 |
| 4,273,682 A | 6/1981 | Kanamori | 252/511 |
| 4,743,274 A | 5/1988 | Ozawa et al. | 51/309 |
| 4,821,135 A | 4/1989 | Nakanishi et al. | 360/132 |
| 4,842,838 A | 6/1989 | Chevallier | 423/339 |
| 4,874,549 A | 10/1989 | Michalchik | 252/511 |
| 4,994,340 A | 2/1991 | Yamazaka et al. | 430/106.6 |
| 5,002,847 A | 3/1991 | Utsumi et al. | 430/137 |
| 5,066,420 A | 11/1991 | Chevallier | 252/313.2 |
| 5,279,807 A | 1/1994 | Moffett et al. | 423/338 |
| 5,691,095 A | 11/1997 | Shinzo et al. | 430/106 |
| 5,726,258 A | 3/1998 | Fischer et al. | 526/64 |
| 5,853,616 A | 12/1998 | Moffett et al. | 252/315.5 |
| 5,869,028 A * | 2/1999 | McGill et al. | 424/49 |
| 6,221,326 B1 | 4/2001 | Amiche | |
| 6,231,955 B1 | 5/2001 | Endo | 428/215 |
| 6,274,112 B1 | 8/2001 | Moffett et al. | 423/338 |
| 6,403,059 B1 | 6/2002 | Martin et al. | 424/49 |
| 6,406,789 B1 | 6/2002 | McDaniel et al. | 428/402 |
| 6,416,917 B1 | 7/2002 | Nakanishi et al. | 430/109.2 |
| 6,419,174 B1 | 7/2002 | McGill et al. | 242/49 |
| 6,616,916 B1 | 9/2003 | Karpe et al. | |
| 6,652,611 B1 | 11/2003 | Huang et al. | 51/307 |
| 6,860,913 B2 | 3/2005 | Huang | 51/307 |
| 6,946,010 B2 | 9/2005 | Huang | 51/307 |
| 7,214,459 B2 | 5/2007 | Iizuka et al. | 430/108.1 |
| 7,255,852 B2 | 8/2007 | Gallis et al. | 424/54 |
| 7,267,814 B2 | 9/2007 | McGill et al. | 424/49 |
| 7,270,803 B1 | 9/2007 | McGill | 424/49 |
| 7,303,742 B2 | 12/2007 | McGill et al. | 424/49 |
| 7,306,788 B2 | 12/2007 | McGill et al. | 424/49 |
| 2006/0110307 A1 | 5/2006 | McGill et al. | 423/338 |
| 2006/0110336 A1 | 5/2006 | McGill et al. | 424/49 |
| 2006/0110338 A1 | 5/2006 | McGill et al. | |
| 2007/0224133 A1 | 9/2007 | McGill | 424/49 |
| 2008/0187498 A1* | 8/2008 | Francis | 424/49 |
| 2009/0048407 A1 | 2/2009 | Barbieri et al. | 526/64 |
| 2009/0053524 A1 | 2/2009 | Yamada et al. | 428/404 |
| 2009/0118478 A1 | 5/2009 | Payne et al. | 534/558 |
| 2011/0206746 A1 | 8/2011 | Hagar et al. | |

FOREIGN PATENT DOCUMENTS

| | | |
|---|---|---|
| DE | 10248799 A1 | 5/2004 |
| EP | 0610136 | 2/1994 |
| EP | 1447433 A1 | 8/2004 |
| WO | WO 96/34592 | 11/1996 |
| WO | WO 96/34593 | 11/1996 |
| WO | WO-97/40105 A1 | 10/1997 |
| WO | WO 01/46073 | 6/2001 |
| WO | WO-03/044100 A1 | 5/2003 |
| WO | WO 03/055802 | 7/2003 |
| WO | WO 2007/064053 | 6/2007 |
| WO | WO-2007/064053 A1 | 6/2007 |
| WO | WO 2009/072218 | 6/2009 |
| WO | WO 2009/140577 | 11/2009 |
| WO | WO-2009/140577 A1 | 11/2009 |

OTHER PUBLICATIONS

Huber Dental Silicas. "Zeodente® 116 Gental Cleaning Dental Silica" J. M. Huber Corporation, Copyright 2010, 4 printed pages.*
International Search Report and Written Opinion issued on Dec. 1, 2011 for Intl. App. No. PCT/US2011/025626, filed on Feb. 21, 2011 (First Inventor—Hagar; Applicant—J.M. Huber Corporation; pp. 1-26).
Barreiros et al. "Calculating Shape Factors from Particle Sizing Data" Part. Part. Syst. Charact. (1996) 13 368-373.
Pabst et al. "Characterization of particles and particle systems," ICT Prague 2007.

(Continued)

*Primary Examiner* — Frederick Krass
*Assistant Examiner* — Isaac Shomer
(74) *Attorney, Agent, or Firm* — Ballard Spahr LLP

(57) ABSTRACT

Disclosed herein is a continuous process for preparing a silica product, comprising: (a) continuously feeding an acidulating agent and an alkali metal silicate into a loop reaction zone comprising a stream of liquid medium; wherein at least a portion of the acidulating agent and the alkali metal silicate react to form a silica product in the liquid medium of the loop reaction zone; (b) continuously recirculating the liquid medium through the loop reaction zone; and (c) continuously discharging from the loop reaction zone a portion of the liquid medium comprising the silica product. Silica products and dentifrice compositions comprising the silica products are also disclosed. A continuous loop reactor is also disclosed.

13 Claims, 12 Drawing Sheets

(56) References Cited

OTHER PUBLICATIONS

Viswanathan et al. "Estimation of Specific Surface Area and Shape Factors" Ind. Eng. Chem. Process Des. Dev. (1982) 21, 345-348.

International Preliminary Report on Patentability issued on Nov. 4, 2012 for for Intl. App. No. PCT/US2011/025626, filed on Feb. 21, 2011 (First Inventor—Hagar; Applicant—J.M. Huber Corporation; pp. 1-11).

International Search Report and Written Opinion issued on Apr. 25, 2012 for Intl. App. No. PCT/US2012/026426, filed on Feb. 24, 2012 (First Inventor—Hagar; Applicant—J.M. Huber Corporation; pp. 1-12).

* cited by examiner

CONTINUOUS SILICA PRODUCTION PROCESS AND SILICA PRODUCT PREPARED FROM SAME

BACKGROUND

Precipitated silica can be prepared by adding an acidulating agent to an alkali metal silicate to precipitate amorphous silica. The resulting precipitate is usually filtered away from the reaction medium and subsequently washed and dried. Typically, the dried silica is then mechanically comminuted in order to provide a suitable particle size and size distribution. On an industrial scale, silica can be prepared by a stepwise batch process that incorporates the aforementioned steps. The equipment needed for such a process can be capital intensive and often leads to inefficiency in the process, particularly when idle time exists when reactants are not being consumed. While various other silica production processes exist, many of these processes are difficult to control and scale-up, and many still require extensive processing steps after the silica has been prepared.

A need therefore exists for improved silica production processes that address the aforementioned shortcomings in traditional silica production processes. This need and other needs are satisfied by the present invention.

SUMMARY

Disclosed herein is a continuous process for preparing a silica product, comprising: (a) continuously feeding an acidulating agent and an alkali metal silicate into a loop reaction zone comprising a stream of liquid medium; wherein at least a portion of the acidulating agent and the alkali metal silicate react to form a silica product in the liquid medium of the loop reaction zone; (b) continuously recirculating the liquid medium through the loop reaction zone; and (c) continuously discharging from the loop reaction zone a portion of the liquid medium comprising the silica product.

Also disclosed are silica particles having an oil absorption value of up to 100 cc/100 g; wherein at least 80% of the silica particles are rounded to well rounded; and wherein the silica particles have a sphericity ($S_{80}$) factor of greater than 0.9 and a Brass Einlehner Abrasion value of less than 8.0 mg lost/100,000 revolutions.

Also disclosed are silica particles having a particle size of from 3 to 15 µm, an oil absorption value of greater than 100 cc/100 g, and a Pellicle Cleaning Ratio (PCR) value at 20% silica loading of at least 85.

Also disclosed are dentifrice compositions comprising silica particles in an amount ranging from 5 to 50% by weight of the composition; wherein the silica particles have an oil absorption value of up to 100 cc/100 g, a sphericity ($S_{80}$) factor of greater than 0.9, and a Brass Einlehner Abrasion value of less than 8.0 mg lost/100,000 revolutions; wherein at least 80% of the silica particles are rounded to well rounded.

Also disclosed are dentifrice compositions comprising silica particles in an amount ranging from 5 to 50% by weight of the composition; wherein the silica particles have a particle size of from 3 to 15 µm, an oil absorption value of greater than 100 cc/100 g, and a Pellicle Cleaning Ratio (PCR) value at 20% silica loading of at least 85.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1:
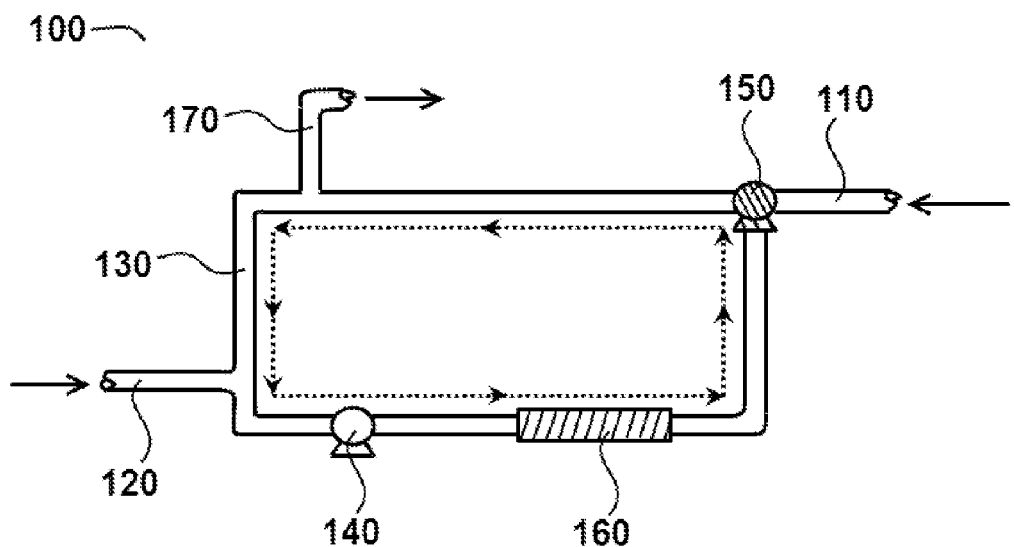
FIG. 1 is a diagram of an exemplary continuous loop reactor.

Before the present compounds, compositions, composites, articles, devices and/or methods are disclosed and described, it is to be understood that the aspects described below are not limited to specific compounds, compositions, composites, articles, devices, methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "an acidulating agent" includes mixtures of two or more such agents, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a number of different acidulating agents and alkali metal silicates are disclosed and discussed, each and every combination and permutation of the acidulating agent and metal silicate are specifically contemplated unless specifically indicated to the contrary. Thus, if a class of agents A, B, and C are disclosed as well as a class of agents D, E, and F and an example of a combination of agents, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Process for Preparing Silica Product

In one aspect, the process of the invention is a continuous process wherein an acidulating agent and an alkali metal silicate are continuously fed into a loop reaction zone comprising a stream of liquid medium; wherein at least a portion of the acidulating agent and the alkali metal silicate react to form a silica product in the liquid medium of the loop reaction zone. As the acidulating agent and alkali metal silicate are continuously fed into the loop reaction zone, the contents of the loop reaction zone (i.e., the liquid medium) are continuously recirculated. Silica product is collected by discharging a portion of the liquid medium that contains the silica product, which in one aspect is equal to the volume of raw materials added to the into the loop reaction zone.

As used herein, the "loop reaction zone" refers to an area inside a reactor that forms a continuous circuit that contains the recirculating liquid medium wherein the acidulating agent and the alkali metal silicate react to form the silica product. As will be discussed below, in one aspect, the loop reaction zone is defined by walls of a continuous loop of one or more loop reactor pipes. Generally, the liquid medium in the loop reaction zone will vary in composition depending on the stage of the process. Prior to adding the acidulating agent and alkali metal silicate into the liquid medium, the medium can contain only water or a suitable aqueous solution or dispersion (slurry). In one aspect, prior to feeding the acidulating agent and the alkali metal silicate into the reaction zone, the liquid medium can contain seed silica, which can serve to reduce gelation in the loop reaction zone and assist in forming the silica product. In a specific aspect, prior to adding acidulating agent and alkali metal silicate, precipitated silica, sodium sulfate, sodium silicate, and water can first be added to the loop reaction zone and recirculated as desired, after which acidulating agent and alkali metal silicate can be added. As acidulating agent and alkali metal silicate are fed into the loop reaction zone, silica product forms in the liquid reaction medium. The silica product will generally be a precipitated product, and thus will be a dispersed phase in the liquid reaction medium. In one aspect, prior to collecting desired silica product, the seed silica product can be purged from the loop reaction zone.

The process temperature and pressure can also vary widely and can depend on what type of silica product is desired. In one aspect of the process, a temperature of from about ambient temperature to about 130° C. is maintained in the liquid medium Likewise, a variety of pressures can be used. The pressure can range from atmospheric pressure to higher pressures. For example, when a continuous loop reactor is used with the process, the reactor can be fitted with a back-pressure valve for controlling a wide range of pressures inside the reactor.

The alkali metal silicate and acidulating agent can be fed into the reaction zone at various rates. The rate of addition of the alkali metal silicate is generally such that a desired concentration of silicate is maintained in the reaction zone, whereas the rate of addition of the acidulating agent is such that a desired pH is maintained in the loop reaction zone. In one aspect, the alkali metal silicate is fed into the loop reaction zone at a rate of at least 0.5 L/min. The maximum alkali metal silicate addition rate will vary widely depending on the volume of the loop reaction zone and scale of the silica production process. A high silicate addition rate could be desired, for example, in a very large scale process wherein a large volume of reactants are being used. In one specific example, the alkali metal silicate is fed at a rate of from 0.5 to 5 L/min, or from 0.5 to 3 L/min.

The acidulating agent is generally fed into the loop reaction zone at a rate sufficient to maintain a pH of from 2.5 to 10.5 in the liquid medium. In other aspects, the acidulating agent is fed into the loop reaction zone at a rate sufficient to maintain a pH of from 7.0 to 10 in the liquid medium, or from 7.0 to 8.5 in the liquid medium. For example, in a specific aspect, a pH of about 7.5 is maintained in the liquid medium. The pH of the liquid medium can be monitored by any conventional pH sensitive electrode. In some examples, the pH of the liquid medium can be evaluated by directly measuring the pH of the liquid medium (slurry). In these examples, the pH of the liquid reaction medium will generally range from 2.5 to 10.5, from 6 to 10, or from 7 to 8.5.

The liquid medium can be recirculated at various rates, depending on the conditions present in the loop reaction zone, such as degree of mixing or shear present in the reaction zone, and depending on the scale of the production process. Generally, the liquid medium is recirculated through the loop reaction zone at a rate of at least 15 L/min. In a specific example, the liquid medium can be recirculated through the loop reaction zone at a rate of from 15 to 100 L/min, from 30 to 80 L/min, or from 70 to 80 L/min.

A variety of acidulating agents can be used, including various acids and other agents capable of reacting with the alkali metal silicate to form the silica product. The acid, or acidulating agent, can be a Lewis acid or Brönsted acid, such as a strong mineral acid, for example, sulfuric acid, hydrochloric acid, nitric acid, phosphoric acid, and so forth. Such acids can be added into the reaction zone as dilute solutions. As a specific example, a 6 to 35% by weight, and more preferably a 10 to 17% by weight solution of sulfuric acid as acidulating agent can be fed into the loop reaction zone. In other aspects, a gas such as $CO_2$, can be used as the acidulating agent. Carbon dioxide produces a weak acid (carbonic acid), and thus it can be desirable for the liquid medium to be kept at a pH target of greater than about 8.5 when such a weak acid is used.

In a further aspect, the acidulating agent can be selected based on the type of silica product that is desired. For example, an acidic solution of aluminum sulfate can be used as the acidulating agent, and the resulting silica product will therefore be an alkali aluminosilicate. As a specific example, aluminum sulfate can be added to sulfuric acid, and this mixture can be used as the acidulating agent.

Any suitable alkali metal silicate can be used with the process of the invention, including both metal silicates, disilicates, and the like. Water soluble potassium silicates and sodium silicates are particularly preferred. In general, acceptable silica products of this invention can be made with silicates having various alkali metal:silicate molar ratios. For a sodium silicate, for example, the molar ratio, $Na_2O:SiO_2$, will generally range from about 1:1 to 1:3.5 and preferably from about 1:2.4 to about 1:3.4. The alkali metal silicate fed into the loop reaction zone is preferably fed as an aqueous solution, similar to the acidulating agent. The alkali silicate solution fed into the loop reaction zone generally can contain between about 8 to 35%, and more preferably between about 8% and 20% by weight alkali metal silicate based on the total weight of the alkali metal silicate solution fed into the loop reaction zone.

When desired, and in order to reduce the alkali silicate or acidulating agent concentration of a source solution, dilution water can be added to the source solution before the solution is fed into the loop reaction zone, and/or the dilution water can be added separately into the loop reaction zone and subsequently mixed with the alkali metal silicate and/or acidulating agent and any other liquid medium contents.

As the desired quantity of acidulating agent and alkali metal silicate are added into the loop reaction zone, the liquid medium will generally be recirculated on average a minimum of three passes through the recirculation zone. The number of times the liquid medium is recirculated through the loop reaction zone, on average, is referred to herein as the "mean number of passes," which is calculated according to the following equations. The residence time of the silica product in the recirculation loop before discharge is calculated by dividing the reaction system volume by the raw material addition rate (alkali metal silicate addition rate+acidulating agent addition rate). The number of passes/minute can then be calculated by dividing the recirculation rate by the total system volume. The residence time can then be multiplied by the number of passes/minute to get the mean number of passes.

$$\text{residence time (min)} = \frac{\text{system volume (L)}}{\text{combined raw material addition rate (L/min)}}$$

$$\text{number of passes/min} = \frac{\text{recirculation rate (L/min)}}{\text{system volume (L)}}$$

$$\text{residence time (min)} \times \frac{\text{number of passes}}{(\text{min})} = \text{mean number of passes}$$

The silica product can be recirculated such that the mean number of passes is from 3 to 200, or from 10 to 200. Generally, the higher the mean number of passes, the more spherical and rounded the silica product becomes. The number of recirculation passes (mean number of passes) can therefore be selected based on the type of silica product that is desired.

Silica product can be discharged from the loop reaction through various mechanisms. In one aspect, a continuous loop reactor is used in the process, as discussed below, which can contain a valve for releasing the silica product from the loop reaction zone. Preferably, however, silica product is displaced from the loop reaction zone by adding additional liquid into the reaction zone such that a portion of the liquid medium containing the silica product is discharged from the reaction zone (i.e., the reaction zone is overflowed). This can be accomplished in one aspect by continuously adding acidulating agent and/or alkali metal silicate into the loop reaction zone as a portion of the liquid medium is volumetrically displaced by the volume of acidulating agent and/or alkali metal silicate that is being added.

In some aspects of the process, the acidulating agent and alkali metal silicate are continuously added while the liquid reaction medium is being recirculated and while silica product is being discharged. Thus, in one aspect, each step of the process occurs continuously and simultaneously. In a further aspect, the acidulating agent and alkali metal silicate are each fed into the loop reaction zone simultaneously. The acidulating agent and alkali metal silicate are preferably added to the loop reaction at different points along the loop reaction zone. For example, alkali metal silicate can be added upstream in the loop relative to the acidulating agent, such that as the acidulating agent is being fed into the reaction zone, alkali metal silicate is already present.

Modifications to the structure of the silica product can be achieved by modifications to temperature, ionic strength, addition rates, and energy input. Generally, changes in temperature, recirculation rate, and acidulating agent/alkali metal silicate addition rates result in the largest changes to the physical properties of the silica products. Generally, the more the liquid medium is recirculated, the longer the residence time of the silica product in the recirculation loop (slower addition rates), and the higher the temperature, the lower the structure (as defined by oil absorption) of the resulting silica product. Manipulations to the pH in the liquid medium were observed to minimize silica deposits (fouling) within the loop reaction zone when a pH of below about 9.0 was used.

The silica product can be collected after being discharged from the loop reaction zone in a suitable vessel and processed as desired. In some aspects, the silica product requires no further processing (other than washing to remove salts, etc.) and can be shipped as a wet cake or can be dried as desired. In one aspect, for example, the resulting silica product can be spray dried according to the methods known in the art. Alternatively, a wet cake of the silica product can be obtained and can be reslurried and handled and supplied in slurry form or supplied as a filter cake, directly. Generally, drying of the silica product described herein can be effected by any conventional equipment used for drying silica, e.g., spray drying, nozzle drying (e.g., tower or fountain), flash drying, rotary wheel drying or oven/fluid bed drying. The dried silica product generally should have a 1 to 15 wt. % moisture level. The nature of the silica reaction product and the drying process both are known to affect the bulk density and liquid carrying capacity.

In other aspects, the silica product can be subjected to various treatments, depending on the nature of the desired silica product. For example, after the silica product is collected, the pH of the silica slurry can be adjusted, e.g., lowered using an acid such as sulfuric acid, following by filtering and washing. In this example, the silica product can be washed to a desired conductivity, for example, from 1500 μS to 2000 μS, followed by drying as discussed above.

To decrease the size of the dried silica product further, if desired, conventional grinding and milling equipment can be used. A hammer or pendulum mill may be used in one or multiple passes for comminuting and fine grinding can be performed by fluid energy or air-jet mill. Products ground to the desired size may be separated from other sizes by conventional separation techniques, e.g., cyclones, classifiers or vibrating screens of appropriate mesh sizing, and so forth.

There are also ways to reduce the particle size of the resulting silica product before isolation and/or during the synthesis of the silica product that affect the size of the dried product or product in slurry form. These include but are not limited to media milling, the use of high shear equipment (e.g., high shear pump or rotor-stator mixers), or ultrasound devices, which in some aspects, can be used during the production process itself, for example in the recirculation loop. Particle size reduction carried out on the wet silica product can be done at anytime before drying.

Silica Product

A variety of types of silica product can be prepared using the disclosed process, depending on the starting materials and process conditions. In one aspect, the silica products of the invention are silica particles having an oil absorption value of up to 100 cc/100 g. In this aspect, at least 80% of the silica particles are rounded to well rounded. These silica particles also have a sphericity ($S_{80}$) factor of greater than 0.9 and a Brass Einlehner Abrasion value of less than 8.0 mg lost/100,000 revolutions.

As used herein "rounded" particles are those having gently rounded corners with flat faces and small reentrants nearly absent. "Well rounded" particles are those having a uniform convex grain outline with no flat faces, corners, or reentrants discernable.

Characterization of the silica particles of the invention as rounded to well rounded is carried out according to the following procedure. A representative sample of silica particles is collected and examined by scanning electron microscopy (SEM). Pictures are taken at two different magnification levels that are representative of the entire image. The first image is taken at a magnification of approximately 200 times and is used to get a sense of the sample homogeneity. Next, an SEM image with a magnification of approximately 20,000 is evaluated. Preferably, there should be a minimum of approximately 20 particles that are shown in the image and care should be taken to insure the picture is representative of the sample as a whole. The particles in this image are then evaluated and characterized by class according to Table 1. At least 80% of the particles of the invention that have oil absorption values up to 100 cc/100 g can be characterized as rounded to well rounded.

TABLE 1

Particle roundness characterization

| Class | Description |
|---|---|
| Angular | Strongly developed faces with sharp corners. Sharply defined, large reentrants with numerous small reentrants. |
| Subangular | Strongly developed flat faces with incipient rounding of corners. Small reentrants subdued and large reentrants preserved. |
| Subrounded | Poorly developed flat faces with corners well rounded. Few small and gently rounded reentrants, and large reentrants weakly defined. |
| Rounded | Flat faces nearly absent with corners all gently rounded. Small reentrants absent. |
| Well Rounded | No flat faces, corners or reentrants discernible, and a uniform convex grain outline. |

Figure 3A:
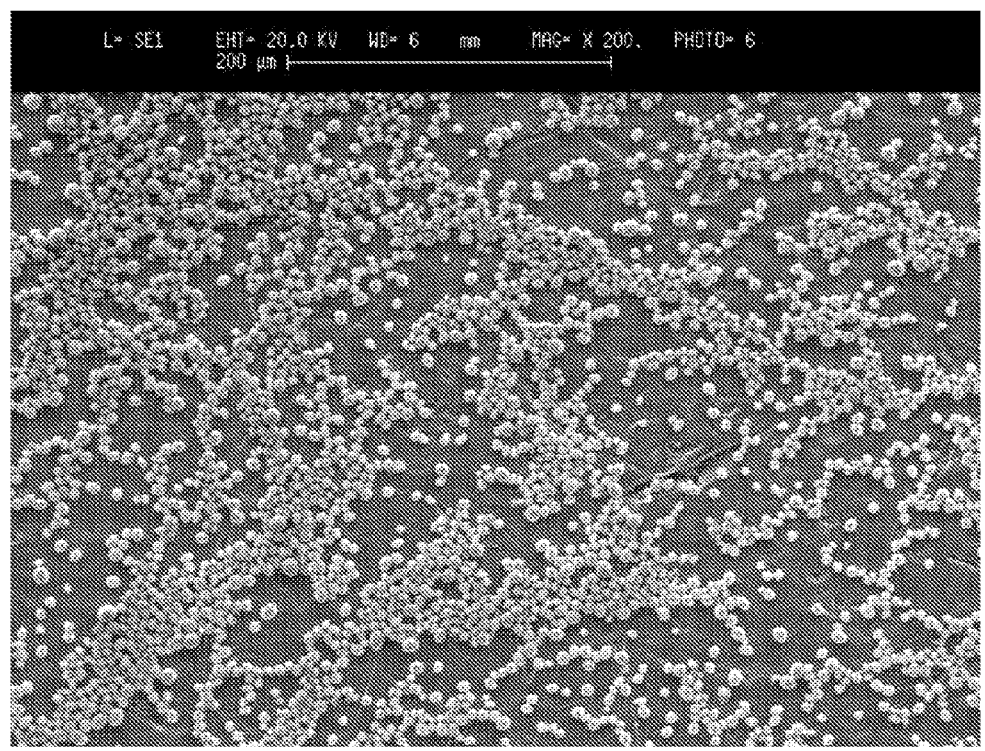
FIGS. 3A and 3B are Scanning Electron Micrographs (SEM) of Example 2D prepared by the disclosed process.
Figure 3B:
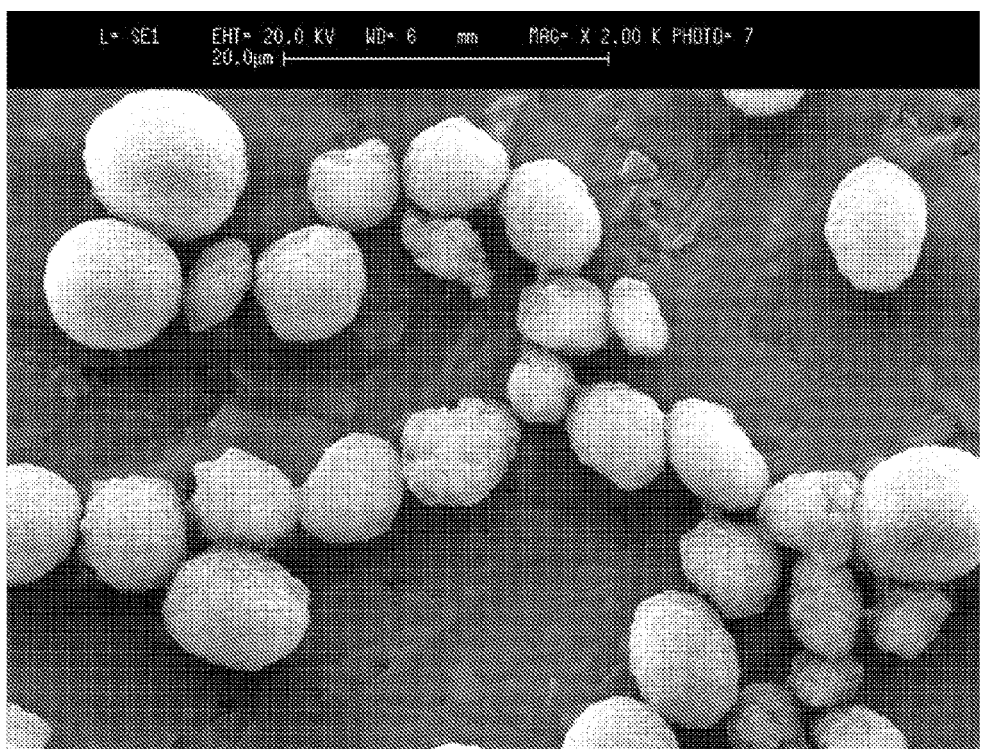
Figure 4A:
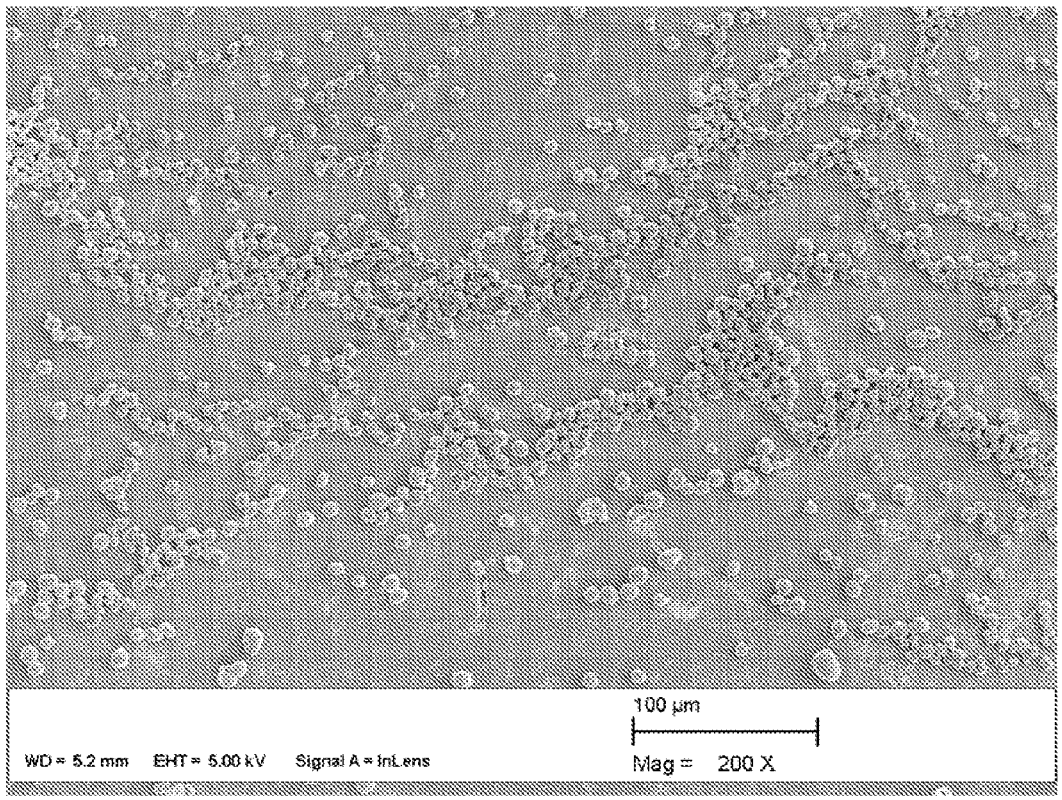
FIGS. 4A and 4B are SEM images of Example 2R prepared by the disclosed process.
Figure 4B:
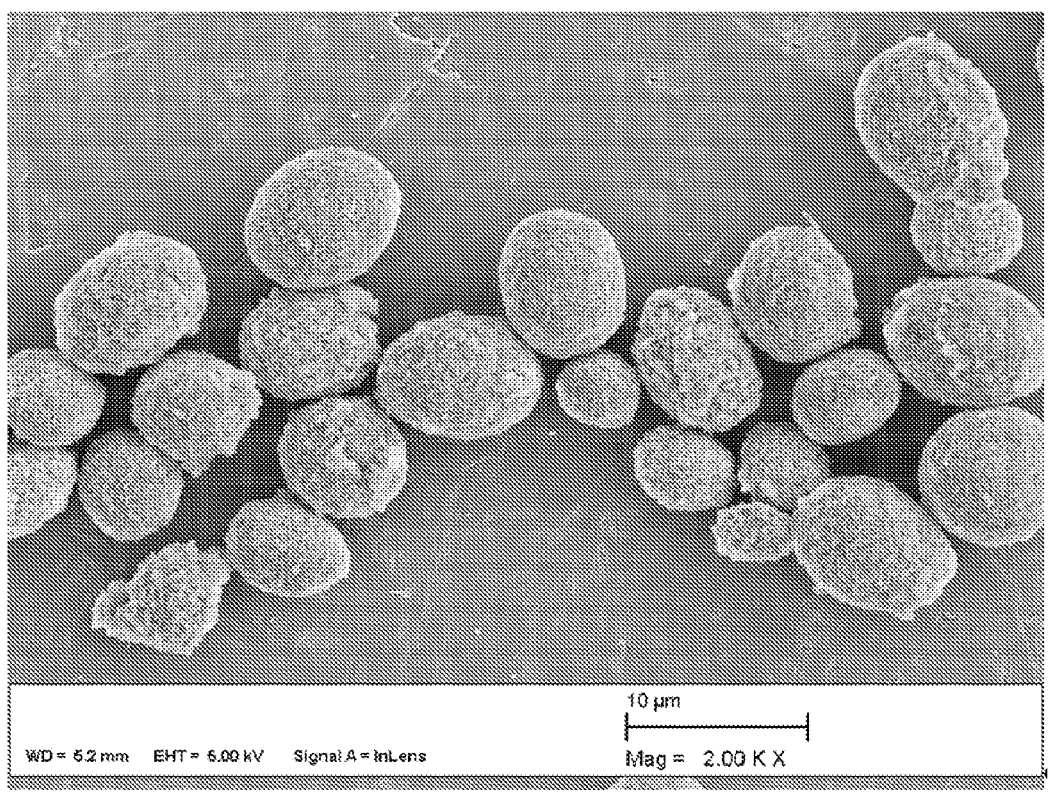
Figure 5A:
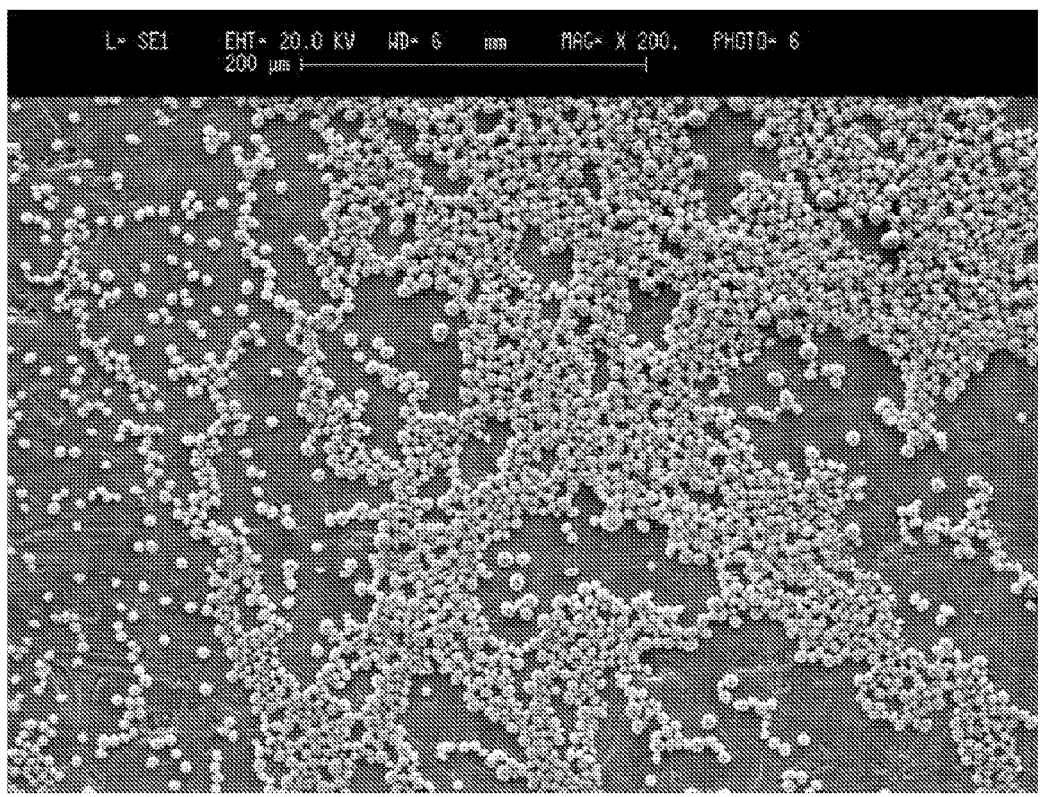
FIGS. 5A and 5B are SEM images of Example 2E prepared by the disclosed process.
Figure 5B:
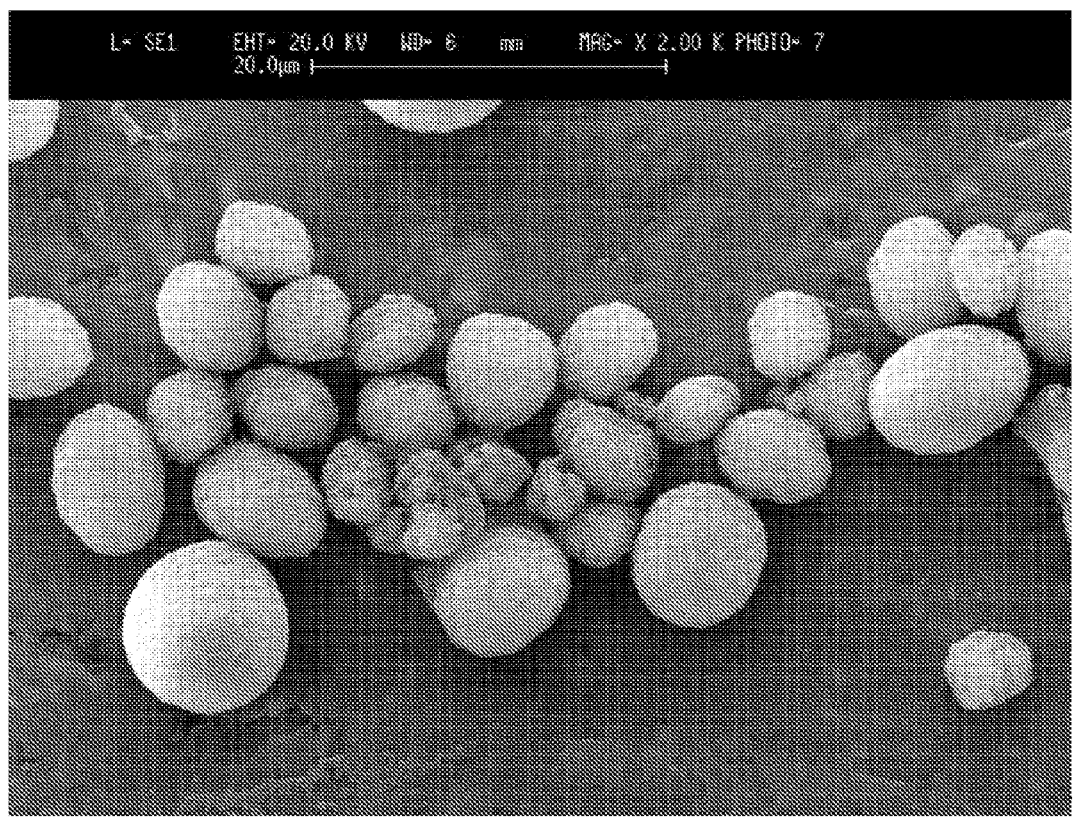
Figure 6A:
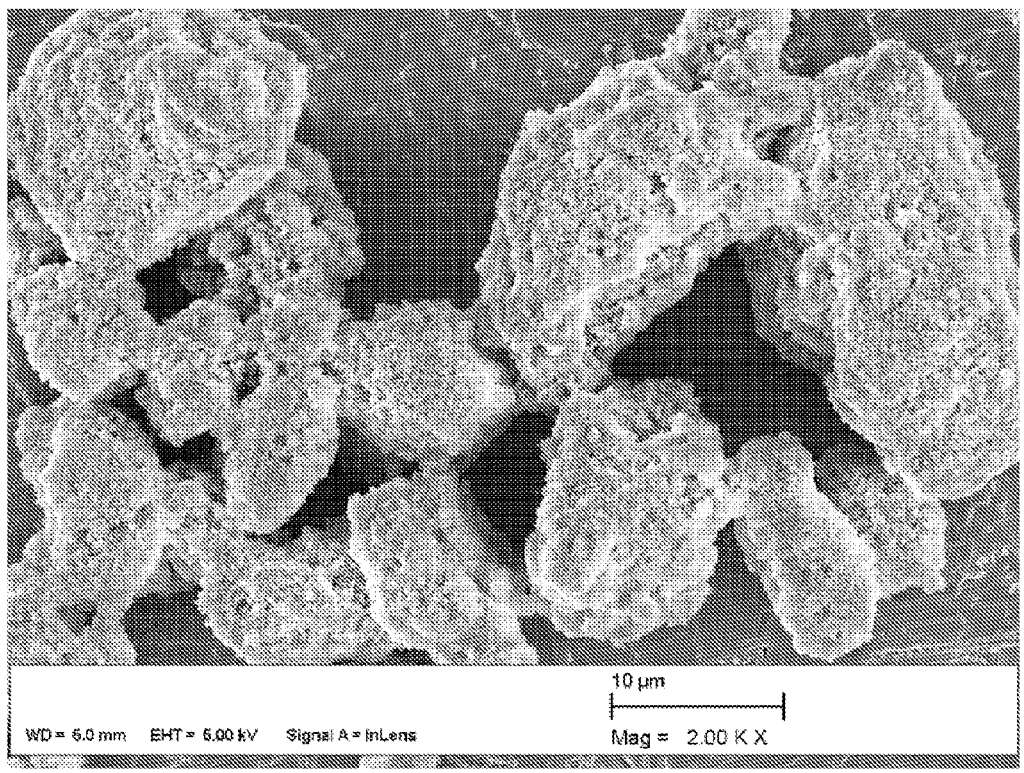
FIGS. 6A and 6B are SEM images of ZEODENT 113 and ZEODENT 165.
Figure 6B:
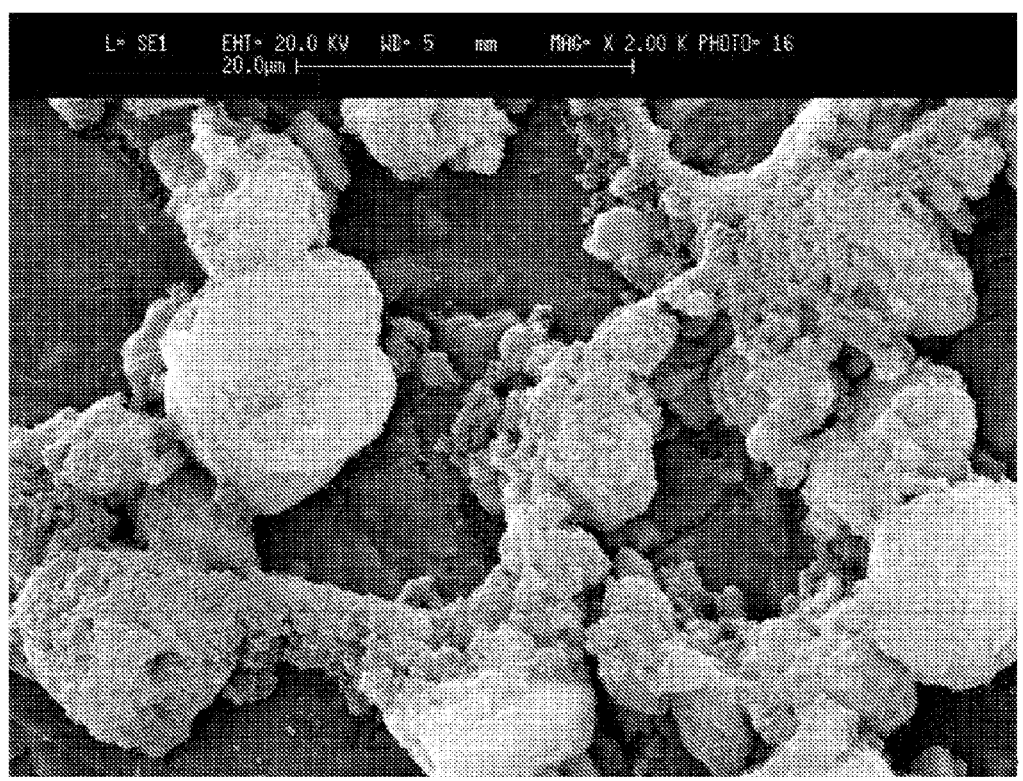
Figure 8:
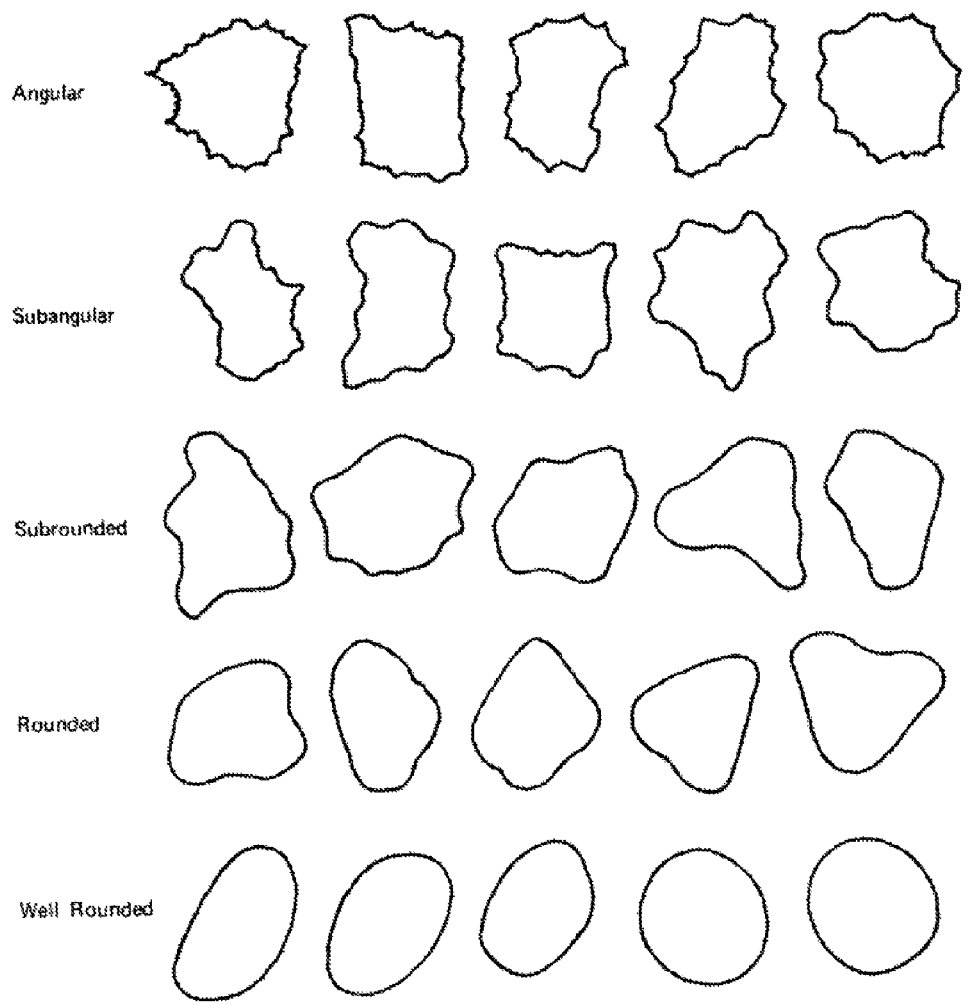
FIG. 8 is a graphical representation of particle roundness.

To assist in characterizing particle roundness, the standard silhouettes graph shown in FIG. 8 can be used. The particles as displayed in the magnified SEM image are compared to the standard particle roundness chart shown in FIG. 8 and classified accordingly. This process is commonly carried out in sedimentation science. As a specific example, the particles shown in FIGS. 3-5, which were prepared by the disclosed process, were classified by comparison to FIG. 8 as rounded to well-rounded in nature, meaning that at least 80% of the particles are rounded to well rounded. In contrast, the silica products shown in FIG. 6, which were prepared by a traditional batch processes, were classified by comparison to FIG. 8 as predominantly angular, sub-angular and sub-rounded, since flat sides and sharp, jagged edges can be observed.

The silica particles of the invention that have oil absorption values of less than 100 cc/100 g can also be characterized according to an index of roundness. As used herein "index of roundness" is defined as the ratio of the radii of curvature of the corners and edges and the radius of the maximum inscribed circle of the particle. Index of roundness can be calculated according to the following equation:

$$\text{Roundess Index} = \frac{(\sum r)/N}{R},$$

wherein r is the radius of curvature of each corner, N is the number of corners, and R is the radius of the maximum inscribed circle in the particle. Each radius of curvature, r, is calculated and summed. This value is then averaged by dividing by the number of corners. The resulting value is then divided by the radius of the maximum inscribed circle, R. This process can be carried out manually or by using commercially available graphical analysis software using an SEM image at 20,000 times magnification.

Figure 9:
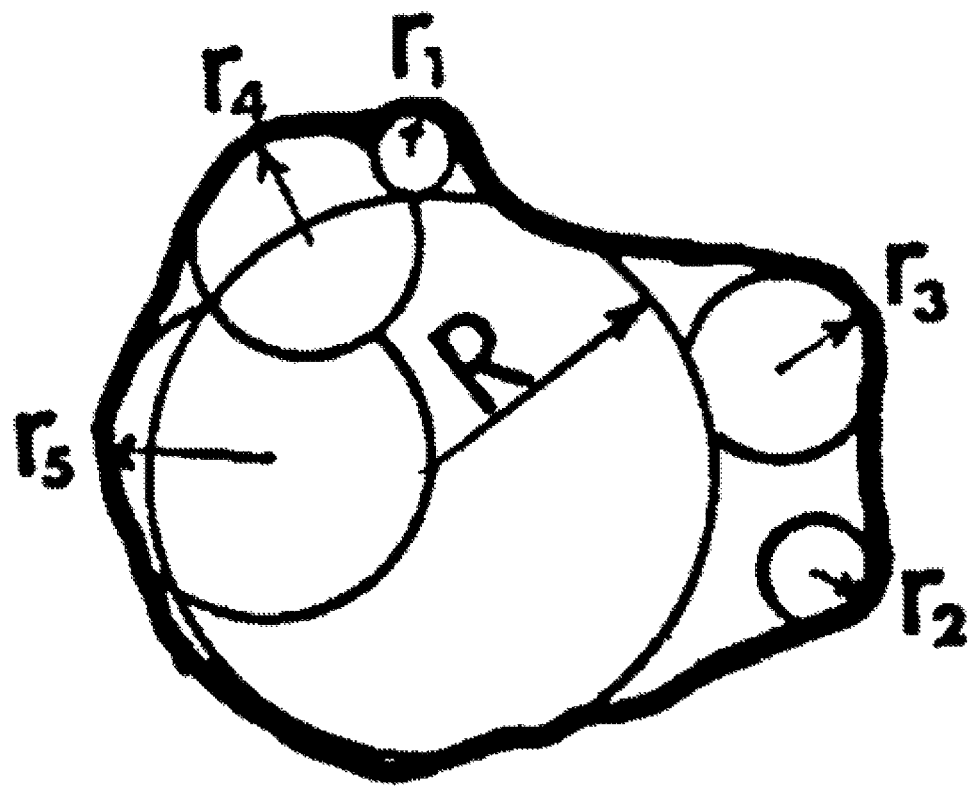
FIG. 9 is a pictorial representation for index of roundness calculations.

With reference to FIG. 9, $r_1 \ldots r_5$ are the radii of the curvature of each corner and R is the radius of the maximum inscribed circle of the particle. As an example, a perfect sphere having an average radius of curvature equal to the radius of the maximum inscribed circle, has a roundness index of 1.0. As the number of edges and faces in the particle increases, the numerator of the equation decreases, and the overall roundness of the particle decreases. Roundness is discussed in detail in "Stratigraphy and Sedimentation," $2^{nd}$ edition by Krumbein and Sloss (1963), which is incorporated herein by this reference for its teachings of roundness.

In one aspect, the silica particles of the invention that have an oil absorption value of up to 100 cc/100 g, wherein at least 80% of the silica particles have a roundness index of at least 0.8, or more preferably at least 0.9. Such silica particles also have a sphericity ($S_{80}$) factor of greater than 0.9 and a Brass Einlehner Abrasion value of less than 8.0 mg lost/100,000 revolutions. At least 80% of these particles can also be classified by comparison to the silhouettes shown in FIG. 8 as rounded to well rounded, as discussed above. The process for calculating index of roundness is as discussed above, i.e., a representative sample having preferably at least 20 particles in an SEM image magnified 20,000 times is evaluated.

The silica particles of the invention that have an oil absorption value of up to 100 cc/100 g also have a sphericity factor ($S_{80}$) of at least 0.9. As used herein, "$S_{80}$" is defined and calculated as follows. An SEM image magnified 20,000 times, which is representative of the silica particle sample, is imported into photo imaging software, and the outline of each particle (two-dimensionally) is traced. Particles that are close in proximity to one another but not attached to one another should be considered separate particles for the evaluation. The outlined particles are then filled in with color, and the image is imported into particle characterization software (e.g., IMAGE-PRO PLUS available from Media Cybernetics, Inc., Bethesda, Md.) capable of determining the perimeter and area of the particles. Sphericity of the particles can then be calculated according to the following equation.

$$\text{Sphericity} = \frac{\text{perimeter}^2}{4\pi \times \text{area}},$$

wherein perimeter is the software measured perimeter derived from the outlined trace of the particles, and wherein area is the software measured area within the traced perimeter of the particles.

The above calculation is carried out for each particle that fits entirely within the SEM image. These values are then sorted by value, and the lowest 20% of these values are discarded. The remaining 80% of these values are averaged to obtain $S_{80}$. As an example, the sphericity factor ($S_{80}$) for the particles shown in FIG. 5 was found to be 0.97.

Figure 7:
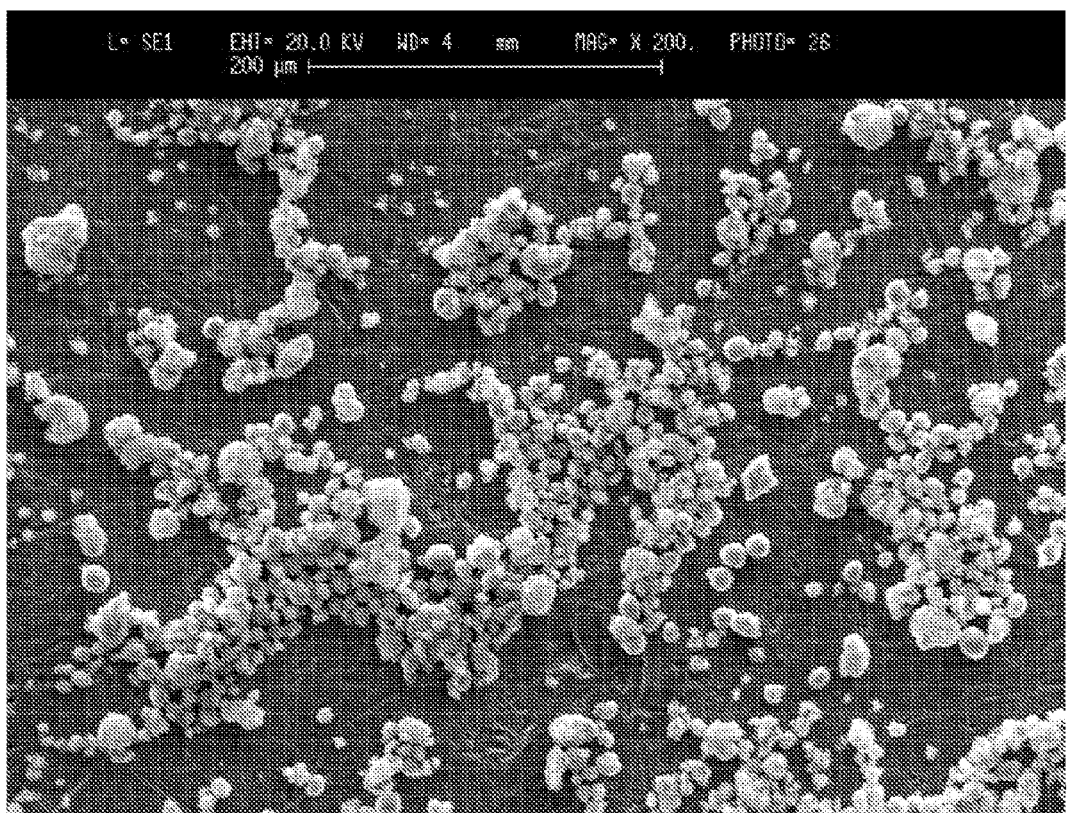
FIG. 7 is a SEM image of Example 2F prepared by the disclosed process.

Silica particles with oil absorption values greater than 100 cc/100 g generally were not observed to have the same high degree of sphericity and roundness as the silica particles discussed above. However, such particles have the ability to build viscosity and also provide superior cleaning performance in dentifrice compositions. An exemplary image of these particles is shown in FIG. 7, which is sample 2F discussed in Example 2 below.

Thus, in a further aspect, the silica particles of the invention can have an oil absorption value of greater than 100 cc/100 g. These particles may not exhibit the same roundness and sphericity as those particles discussed above, which have oil absorption values of up to 100 cc/100 g. However, the silica particles having an oil absorption value of greater than 100 cc/100 g are characterized as having a particle size of from 3 to 15 μm and will generally exhibit a Pellicle Cleaning Ratio (PCR) value at 20% silica loading of at least 85, for example from 85 to 120.

The silica particles of the invention are also characterized by a number of other properties, which are discussed below. The following characteristic properties refer to both the particles having oil absorption values up to 100 cc/100 g and greater than 100 cc/100 g, unless otherwise noted.

Median particle sizes of the silica particles of the invention were determined at various stages during the process and after or before various particle treatment steps. As used herein, median particle size, average particle size (APS), and $D_{50}$, is referred to herein as the particle size for which 50% of the sample has a smaller size and 50% of the sample has a larger size.

In one aspect, the silica particles of the invention have a median particle size while present in the liquid reaction medium of from 3 to 10 preferably from 3 to 8 and more preferably from 4 to 6 μm. In specific examples, the median particle size of the silica particles in the liquid reaction medium is from 5 to 6 μm. To determine median particle size of the particles in the liquid reaction medium, an aliquot of the liquid reaction medium can be removed from the recirculating reaction zone, for example through volumetric displacement, and the particles in the aliquot can be analyzed.

After discharging the silica product from the loop reaction zone and drying the silica product, but prior to any milling step, the resulting silica particles have a median particle size of from 3 to 25 μm. In some examples, the silica particles have a median particle size after drying but prior to milling of from 3 to 15 μm. In further examples, the silica particles have a median particle size after drying but prior to milling of from 4 to 8 μm.

Milling can be used to reduce the particle size of the dried silica particles, as discussed above. For example, after Raymond milling or air milling, the silica particles will generally have a median particle size of from 3 to 10 μm. In specific examples, the silica particle have a particle size after milling (including Raymond milling and/or air milling) of from 3 to 7 μm or even from 5 to 7 μm.

Generally, it was observed that the dry particle size, sphericity, and roundness of the particles was related to the structure of the silica. As the structure was lowered, a higher percentage of well rounded/higher sphericity particles with little change to the liquid reaction medium (slurry) particle size distribution resulted upon drying. As the structure was increased, the level of well rounded particles/higher sphericity decreased, and the average particle size increased upon drying. Higher structure samples can be reduced to their slurry particle sizes with gentle Raymond milling. More intense Raymond milling and also air milling did not substantially reduce the particle size much smaller than the slurry particle size. Milling of low structure products did not result in much of a change in particle size. Structure of the silica particles generally refers to oil absorption capacity. A low structure silica therefore has low oil absorption capacity, whereas a high structure silica has a high oil absorption capacity.

Median particle size was determined using a Model LA-930 (or LA-300 or an equivalent) laser light scattering instrument available from Horiba Instruments, Boothwyn, Pa.

Generally, the silica particles of the invention have narrow particle size distributions. Particle size distribution can be evaluated based on a number of parameters, including coefficient of uniformity, coefficient of curvature, and distribution symmetry. Coefficient of uniformity (Cu) is defined as $D_{60}/D_{10}$. Coefficient of curvature (Cc) is defined as $(D_{30}/(D_{10} \times D_{60}))$. The peak symmetry can also be defined as $(D_{90}-D_{50})/(D_{50}-D_{10})$, wherein a shape value of 1.0 would represent a perfectly symmetrical curve. Coefficients of uniformity of the silica particles generally range from 1.8 to 2.5. Coefficients of curvature generally range from 0.2 to 0.31, while curve shape values generally range from 1.3 to 1.7. In specific examples, peak symmetries ranged from 1.3 to 1.5, indicating a very symmetrical distribution of silica particles.

The silica particles of the invention have water absorption values ranging from 57 to 272 cc water per 100 g of silica, although water absorption values can be made even higher. Water absorption values are determined with an Absorptometer "C" torque rheometer from C.W. Brabender Instruments, Inc. Approximately ⅓ of a cup of silica (or silicate) is transferred to the mixing chamber of the Absorptometer, and it is mixed at 150 rpm. Water then is added at a rate of 6 ml/min, and the torque required to mix the powder is recorded. As the water is absorbed by the powder, the torque will reach a maximum as the powder transforms from a free flowing powder to a paste. The total volume of water added when the maximum torque has been achieved is then standardized to the quantity of water that can be absorbed by 100 g of powder. Since the powder is used on an as received basis (it is not previously dried), the free moisture value of the powder is used to calculate a "moisture corrected water AbC value" by the following equation.

$$\text{Water Absorption} = \frac{\text{water absorbed }(cc) + \% \text{ moisture}}{(100(g) - \% \text{ moisture})/100}$$

The Absorptometer is commonly used to determine the oil number of carbon black in compliance with ASTM D 2414 methods B and C and ASTM D 3493.

As discussed above, in one aspect, the silica particles of the invention have oil absorption values of up to 100 cc/100 g, for example 30 to 100 cc/100 g, whereas in a further aspect, the silica particles have oil absorption values of greater than 100 cc/100 g, for example, ranging from greater than 100 cc/100 g to 150 cc/100 g. Generally, the silica particles of the invention were observed to have oil absorption capacities ranging from 30 to 171 cc ($cm^3$ or mL) of oil absorbed per 100 g of silica.

Oil absorption values were measured using the rub-out method (ASTM D281). This method is based on a principle of mixing linseed oil with silica by rubbing the linseed oil/silica mixture with a spatula on a smooth surface until a stiff putty-like paste is formed. By measuring the quantity of oil required to have a paste mixture which will curl when spread out, the oil absorption value of the silica can be calculated, which represents the volume of oil required per unit weight of silica to saturate the silica sorptive capacity. A higher oil absorption level indicates a higher structure of silica. A low value is indicative of what is considered a low-structure silica. The oil absorption value can be determined from the following equation.

$$\text{Oil Absorption} = \frac{cc \text{ oil absorbed}}{\text{wt. silica (g)}} \times 100 = \frac{cc \text{ oil absorbed}}{100 \text{ g silica}}$$

The silica particles of the invention generally exhibit a BET surface area ranging from 10 to 425 $m^2/g$. In specific examples, the silica particles exhibit a BET surface area ranging from 10 to 300 $m^2/g$, and preferably from 50 to 350 $m^2/g$. The BET surface areas of the disclosed silica particles was determined by the BET nitrogen adsorption method of Brunaur et al., J. Am. Chem. Soc., 60, 309 (1938), which is incorporated herein by reference for its teaching of the BET surface area measurement.

The CTAB surface area of the disclosed silica particles generally ranges from 10 to 250 $m^2/g$, and in some examples from 50 to 200 $m^2/g$. CTAB surface area of silica is determined by absorption of CTAB (cetyltrimethylammonium bromide) on the silica surface, the excess separated by centrifugation and the quantity determined by titration with sodium lauryl sulfate using a surfactant electrode. Specifically, about 0.5 g of silica is placed in a 250-ml beaker with 100.00 ml CTAB solution (5.5 g/L), mixed on an electric stir plate for 1 hour, then centrifuged for 30 minutes at 10,000 rpm. One ml of 10% Triton X-100 is added to 5 ml of the clear supernatant in a 100-ml beaker. The pH is adjusted to 3.0-3.5 with 0.1N HCl and the specimen is titrated with 0.0100 M sodium lauryl sulfate using a surfactant electrode (Brinkmann SUR1501-DL) to determine the endpoint.

The mercury (Hg) intruded volume of the disclosed silica particles generally ranges from 0.5 to 3 mL/g. The mercury intruded volume or total pore volume (Hg) is measured by mercury porosimetry using a Micromeritics Autopore II 9220 apparatus. The pore diameters can be calculated by the Washburn equation employing a contact angle Theta ($\Theta$) equal to 130° and a surface tension gamma equal to 485 dynes/cm. Mercury is forced into the voids of the particles as a function of pressure and the volume of the mercury intruded per gram of sample is calculated at each pressure setting. Total pore volume expressed herein represents the cumulative volume of mercury intruded at pressures from vacuum to 60,000 psi.

Increments in volume ($cm^3/g$) at each pressure setting are plotted against the pore radius or diameter corresponding to the pressure setting increments. The peak in the intruded volume versus pore radius or diameter curve corresponds to the mode in the pore size distribution and identifies the most common pore size in the sample. Specifically, sample size is adjusted to achieve a stem volume of 25-75% in a powder penetrometer with a 5 mL bulb and a stem volume of about 1.1 mL. Samples are evacuated to a pressure of 50 µm of Hg and held for 5 minutes. Mercury fills the pores from 1.5 to 60,000 psi with a 10 second equilibrium time at each of approximately 103 data collection points.

An aqueous solution of the silica particles of the invention will generally exhibit a Brass Einlehner Abrasion (BEA) value of less than 10 mg lost per 100,000 revolutions, preferably less than 8 mg lost per 100,000 revolutions, and more preferably less than 5 mg lost per 100,0000 revolutions. The BEA value will typically be at least 1. Specific ranges of BEA values include 1 to 10, 1 to 8, 1 to 7, and 1 to 5 mg lost per 100,000 revolutions.

The Brass Einlehner Abrasion (BEA) test used to measure the hardness of the silica products of the invention is described in detail in U.S. Pat. No. 6,616,916 to Karpe et al., which is incorporated herein by reference for its teaching of the BE Abrasion test. Generally, the test involves an Einlehner AT-1000 Abrader used as follows: (1) a Fourdrinier brass wire screen is weighed and exposed to the action of a 10% aqueous silica suspension for a fixed length of time; (2) the amount of abrasion is then determined as milligrams brass lost from the Fourdrinier wire screen per 100,000 revolutions. The result, measured in units of mg loss, can be characterized as the 10% brass Einlehner (BE) abrasion value.

Technidyne brightness values of the silica particles generally range from 95 to 100. In specific examples, Technidyne brightness values range from 97 to 100, or even 98 to 100. To measure brightness, fine powder silica is pressed into a smooth surfaced pellet and analyzed using a Technidyne Brightmeter S-5/BC. This instrument has a dual beam optical system where the sample is illuminated at an angle of 45°, and the reflected light is viewed at 0°. It conforms to TAPPI test methods T452 and T646, and ASTM Standard D985. Powdered materials are pressed to about a 1 cm pellet with enough pressure to give a pellet surface that is smooth and without loose particles or gloss.

Dispersions of the disclosed silica particles will generally have a refractive index (RI) value greater than 1.4. In some examples, a dispersion of the disclosed silica particles have an RI value of from 1.4 to 1.5. The dispersions generally have a % Transmission value (% T) ranging from 20 to 75.

To measure refractive index and degree of light transmission, a range of glycerin/water stock solutions (about 10) was prepared so that the refractive index of these solutions lies between 1.428 and 1.460. Typically, these stock solutions will cover the range of 70 wt % to 90 wt % glycerin in water. To determine the RI, one or two drops of each standard solution is separately placed on the fixed plate of a refractometer (Abbe 60 Refractometer Model 10450). The covering plate is fixed and locked into place. The light source and refractometer are switched on and the refractive index of each standard solution is read.

Into separate 20-ml bottles, 2.0+/−0.01 ml of the disclosed silica product was added to 18.0+/−0.01 ml of each respective stock glycerin/water solution (for products with measured oil absorption above 150, the test uses 1.0 g of disclosed silica product and 19.0 g of the stock glycerin/water solution). The bottles were then shaken vigorously to form a silica dispersion, the stoppers were removed from the bottles, and the bottles were placed in a desiccator, which was then evacuated with a vacuum pump (about 24 inches Hg).

The dispersions were then de-aerated for 120 minutes and visually inspected for complete de-aeration. The "% T" at 590 nm (Spectronic 20 D+) was measured after the samples returned to room temperature (about 10 minutes), according to the manufacturer's operating instructions. The % T was measured on the disclosed silica product by placing an aliquot of each dispersion in a quartz cuvette and reading the % T at 590 nm wavelength for each sample on a 0-100 scale. The % Transmittance vs. RI of the stock solutions was plotted on a curve. The RI of the silica was defined as the position of the plotted peak maximum (the ordinate or X-value) on the % T vs. the RI curve. The Y-value (or abscissa) of the peak maximum was the % T.

The silica particles can be filtered and washed with water to reduce the sodium sulfate levels (when present) to tolerable levels. Washing of the reaction product is generally conducted after filtering. The pH of the washed wet cake can be adjusted, if necessary, prior to proceeding to subsequent steps described herein. Sodium sulfate content of the silica particles of the invention can be up to about 6%. Sodium sulfate content was measured by conductivity of a known concentration of silica slurry. Specifically, 38 g silica wet cake sample was weighed into a one-quart mixer cup of a Hamilton Beach Mixer, model Number 30, and 140 ml of deionized water was added. The slurry was mixed for 5 to 7 minutes, then the slurry was transferred to a 250-ml graduated cylinder and the cylinder filled to the 250-ml mark with deionized water, using the water to rinse out the mixer cup. The sample was mixed by inverting the graduated cylinder (covered) several times. A conductivity meter, such as a Cole Parmer CON 500 Model #19950-00, was used to determine the conductivity of the slurry. Sodium sulfate content was determined by comparison of the sample conductivity with a standard curve generated from a known method-of-addition sodium sulfate/silica composition slurries.

Dentifrice Compositions

The silica product of the invention are particularly useful in dentifrice compositions as part or all of the abrasive or cleaning agent. As used herein, a "dentifrice composition" refers to a composition that can be used to maintain oral hygiene, for example by cleaning accessible surfaces of the teeth. The dentifrice composition can be a liquid, powder, or paste. Typically, the dentifrice compositions are primarily composed of water, detergent, humectant, binder, flavoring agents, and a finely powdered abrasive (the disclosed silica product). The silica particles of the invention, when incorporated into dentifrice compositions, can be present at a level of from about 5% to about 50% by weight, preferably from about 10% to about 50% by weight, and more preferably from about 10% to about 35% by weight. As a specific example, the dentifrice composition can comprise the silica particles present at about 20% by weight.

Exemplary oral dentifrice or oral cleaning formulations can comprise any one or more of the following ingredients in any suitable amount, for example, in the following amounts (% by weight). The silica thickener in the below example can be any thickener known in the art, such as ZEODENT products as discussed below, and/or can include silica particles of the invention. The abrasive preferably contains silica particles of the invention in the amounts shown in Table 2.

TABLE 2

Ingredients and relative amounts in an exemplary dentifrice composition.
Exemplary Dentifrice Composition

| Ingredient | Amount (% by weight) |
|---|---|
| humectant(s) (total) | 5-70 |
| Deionized water | 5-70 |
| Binder | 0.5-2.0 |
| Therapeutic agent | 0.1-2.0 |
| Chelating agent | 0.4-10 |
| Thickener | 0-15 |
| Surfactant | 0.5-15 |
| Abrasive | 10-50 |
| Sweetening agent | <1.0 |
| Coloring agent | <1.0 |
| Flavoring agent | <5.0 |
| Preservative | <0.5 |

The disclosed silica particles can be utilized alone as the abrasive in the dentifrice composition, or as an additive or co-abrasive with other abrasive materials discussed herein or known in the art. Thus, any number of other conventional types of abrasive additives can be present within the dentifrice compositions of the invention. Other such abrasive particles include, for example, precipitated calcium carbonate (PCC), ground calcium carbonate (GCC), chalk, bentonite, dicalcium phosphate or its dihydrate forms, silica gel (by itself, and of any structure), precipitated silica, amorphous precipitated silica (by itself, and of any structure as well), perlite, titanium dioxide, dicalcium phosphate, calcium pyrophosphate, alumina, hydrated alumina, calcined alumina, aluminum silicate, insoluble sodium metaphosphate, insoluble potassium metaphosphate, insoluble magnesium carbonate, zirconium silicate, particulate thermosetting resins and other suitable abrasive materials. Such materials can be introduced into the dentifrice compositions to tailor the polishing characteristics of the target formulation.

In addition to the abrasive component, the dentifrice can also contain one or more organoleptic enhancing agents. Organoleptic enhancing agents include humectants, sweeteners, surfactants, flavorants, colorants and thickening agents, (also sometimes known as binders, gums, or stabilizing agents).

Humectants serve to add body or "mouth texture" to a dentifrice as well as preventing the dentifrice from drying out. Suitable humectants include polyethylene glycol (at a variety of different molecular weights), propylene glycol, glycerin (glycerol), erythritol, xylitol, sorbitol, mannitol, lactitol, and hydrogenated starch hydrolyzates, and mixtures thereof. In specific examples, humectants are present in an amount from about 20 wt % to about 50 wt % of the dentifrice composition, for example 40%.

Sweeteners can be added to the dentifrice composition (e.g., toothpaste) to impart a pleasing taste to the product. Suitable sweeteners include saccharin (as sodium, potassium or calcium saccharin), cyclamate (as a sodium, potassium or calcium salt), acesulfame-K, thaumatin, neohesperidin dihydrochalcone, ammoniated glycyrrhizin, dextrose, levulose, sucrose, mannose, and glucose.

Surfactants can be used in the dentifrice compositions of the invention to make the compositions more cosmetically acceptable. The surfactant is preferably a detersive material which imparts to the composition detersive and foaming properties. Suitable surfactants are safe and effective amounts of anionic, cationic, nonionic, zwitterionic, amphoteric and betaine surfactants such as sodium lauryl sulfate, sodium dodecyl benzene sulfonate, alkali metal or ammonium salts of lauroyl sarcosinate, myristoyl sarcosinate, palmitoyl sarcosinate, stearoyl sarcosinate and oleoyl sarcosinate, polyoxyethylene sorbitan monostearate, isostearate and laurate, sodium lauryl sulfoacetate, N-lauroyl sarcosine, the sodium, potassium, and ethanolamine salts of N-lauroyl, N-myristoyl, or N-palmitoyl sarcosine, polyethylene oxide condensates of alkyl phenols, cocoamidopropyl betaine, lauramidopropyl betaine, palmityl betaine and the like. Sodium lauryl sulfate is a preferred surfactant. The surfactant is typically present in the oral care compositions of the present invention in an amount of about 0.1 to about 15% by weight, preferably about 0.3% to about 5% by weight, such as from about 0.3% to about 2.5%, by weight.

Flavoring agents can also be added to dentifrice compositions. Suitable flavoring agents include, but are not limited to, oil of wintergreen, oil of peppermint, oil of spearmint, oil of sassafras, and oil of clove, cinnamon, anethole, menthol, thymol, eugenol, eucalyptol, lemon, orange and other such flavor compounds to add fruit notes, spice notes, etc. These flavoring agents generally comprise mixtures of aldehydes, ketones, esters, phenols, acids, and aliphatic, aromatic and other alcohols.

Colorants can be added to improve the aesthetic appearance of the product. Suitable colorants include without limitation those colorants approved by appropriate regulatory bodies such as the FDA and those listed in the European Food and Pharmaceutical Directives and include pigments, such as $TiO_2$, and colors such as FD&C and D&C dyes.

Thickening agents are useful in the dentifrice compositions to provide a gelatinous structure that stabilizes the toothpaste against phase separation. Suitable thickening agents include silica thickener; starch; glycerite of starch; gums such as gum karaya (sterculia gum), gum tragacanth, gum arabic, gum ghatti, gum acacia, xanthan gum, guar gum and cellulose gum; magnesium aluminum silicate (Veegum); carrageenan; sodium alginate; agar-agar; pectin; gelatin; cellulose compounds such as cellulose, carboxymethyl cellulose, hydroxyethyl cellulose, hydroxypropyl cellulose, hydroxymethyl cellulose, hydroxymethyl carboxypropyl cellulose, methyl cellulose, ethyl cellulose, and sulfated cellulose; natural and synthetic clays such as hectorite clays; and mixtures thereof. Typical levels of thickening agents or binders are from about 0 wt % to about 15 wt % of a toothpaste composition.

Useful silica thickeners for utilization within a toothpaste composition, for example, include, as a non-limiting example, an amorphous precipitated silica such as ZEODENT 165 silica. Other preferred (though non-limiting) silica thickeners are ZEODENT 153, 163 and/or 167 and ZEOFREE, 177, and/or 265 silica products, all available from J. M. Huber Corporation.

Therapeutic agents can also be used in the compositions to provide for the prevention and treatment of dental caries, periodontal disease and temperature sensitivity. Examples of therapeutic agents, without intending to be limiting, are fluoride sources, such as sodium fluoride, sodium monofluorophosphate, potassium monofluorophosphate, stannous fluoride, potassium fluoride, sodium fluorosilicate, ammonium fluorosilicate and the like; condensed phosphates such as tetrasodium pyrophosphate, tetrapotassium pyrophosphate, disodium dihydrogen pyrophosphate, trisodium monohydrogen pyrophosphate; tripolyphosphates, hexametaphosphates, trimetaphosphates and pyrophosphates, such as; antimicrobial agents such as triclosan, biguanides, such as alexidine, chlorhexidine and chlorhexidine gluconate; enzymes such as papain, bromelain, glucoamylase, amylase, dextranase, mutanase, lipases, pectinase, tannase, and proteases; quaternary ammonium compounds, such as benzalkonium chloride (BZK), benzethonium chloride (BZT), cetylpyridinium chloride (CPC), and domiphen bromide; metal salts, such as zinc citrate, zinc chloride, and stannous fluoride; sanguinaria extract and sanguinarine; volatile oils, such as eucalyptol, menthol, thymol, and methyl salicylate; amine fluorides; peroxides and the like. Therapeutic agents may be used in dentifrice formulations singly or in combination at a therapeutically safe and effective level.

Preservatives can also added to the compositions of the present invention to prevent bacterial growth. Suitable preservatives approved for use in oral compositions such as methylparaben, propylparaben and sodium benzoate can be added in safe and effective amounts.

The dentifrices disclosed herein can also a variety of additional ingredients such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, and the like.

The dentifrice composition also typically comprises a solvent, which is usually water. Generally, water provides the balance of the composition in addition to the additives mentioned above. The water is preferably deionized and free of impurities. The dentifrice will usually comprise from about 5 wt % to about 70 wt % of water, for example 5 wt % to 35 wt %, such as 11% water.

A specific example of a disclosed dentifrice composition is one that comprises 10-50% by weight of disclosed silica particles, Glycerin, Sorbitol, Water, CARBOWAX 600, CEKOL, Tetrasodium Pyrophosphate, Sodium Saccharin, Sodium Fluoride, ZEODENT, Titanium Dioxide, Sodium Lauryl Sulfate, a flavor, and an optional colorant.

The dentifrice compositions disclosed herein can be evaluated using a variety of measurements. The cleaning property of dentifrice compositions is typically expressed in terms of Pellicle Cleaning Ratio ("PCR") value. The PCR test measures the ability of a dentifrice composition to remove pellicle film from a tooth under fixed brushing conditions. The PCR test is described in "In Vitro Removal of Stain With Dentifrice" G. K. Stookey, et al., J. Dental Res., 61, 1236-9, 1982, which is incorporated herein by reference for its teaching of PCR. Generally, the dentifrice compositions of the invention have a PCR value of at least 85 at loading levels of 20%, for example, from about 85 to about 107.

The Radioactive Dentin Abrasion (RDA) of the dentifrice compositions of the invention will generally be at least 100, for example from about 100 to about 315. RDA values of dentifrices containing the silica particles used in this invention are determined according to the method set forth by Hefferen, Journal of Dental Res., July-August 1976, 55 (4), pp. 563-573, and described in Wason U.S. Pat. Nos. 4,340,583, 4,420,312 and 4,421,527, which are each incorporated herein by reference for their teaching of RDA measurements. Both PCR and RDA results vary depending upon the nature and concentration of the components of the dentifrice composition. PCR and RDA values are unitless.

The toothpaste (dentifrice) viscosity of the disclosed dentifrice compositions varies and can be measured utilizing a Brookfield Viscometer Model RVT equipped with a Helipath T-F spindle and set to 5 rpm by measuring the viscosity of the toothpaste at 25° C. at three different levels as the spindle descends through the toothpaste test sample and averaging the results. Brookfield viscosity is expressed in centipoise (cP).

Continuous Loop Reactor

The process of the invention, in various aspects, can be carried out using a continuous loop reactor or a pipe reactor.

A suitable continuous loop reactor generally comprises an inlet port for the acidulating agent, an inlet port for the alkali metal silicate, and a product discharge port all in fluid communication with a continuous loop defined by one or more pipes. The liquid medium in the continuous loop can be recirculated using a variety of means, such as a pump that is in the loop itself. Other components of the continuous loop reactor can include without limitation a heat exchanger in the loop for controlling temperature in the liquid medium, a back-pressure valve for controlling pressure, and/or an in-line mixing device in the loop for mixing the contents of the liquid reaction medium.

With reference to FIG. 1, an exemplary continuous loop reactor 100 comprises an acidulating agent inlet port 110 for introducing the acidulating agent into the liquid medium of the loop reaction zone and an alkali metal silicate inlet port 120 for introducing the alkali metal silicate in the loop reaction zone. The loop reaction zone is defined by one or more pipes 130 that define a continuous loop. Various other components can also be present in the continuous loop reactor 100, including a pump 140 for recirculating the liquid medium through the one or more pipes 130. During the process of the invention, the pump 140 should be in liquid communication with the liquid reaction medium. The continuous loop can also be in fluid communication with an in-line mixing device 150. In the example shown in FIG. 1, the in-line mixing device 150 is also in fluid communication with the acidulating agent inlet port, and serves to both facilitate entry of the acidulating agent into the continuous loop and also to mix the liquid medium inside the loop reaction zone. A heat exchanger 160 can also be present for controlling the temperature of the liquid medium in the continuous loop. The heat exchanger 160 is thus in thermal communication with the one or more pipes 130 that define the continuous loop. As acidulating agent, alkali metal silicate, or another liquid as discussed above, are continuously added to the reaction, the liquid medium will overflow from the continuous loop and exit the loop reaction zone through product discharge port 170. The product is then collected. In a specific aspect, the reaction can be fitted with one or more pressure controlling devices in fluid communication with the one or more pipes 130, such as a back-pressure valve (not shown) for regulating the pressure inside the loop reactor.

Any suitable pump 140 can be used with the loop reactor. The in-line mixing device 150 is used in part to provide a high shear environment to the recirculating liquid medium and is preferably is a rotor/stator type in-line mixer. Examples of useful rotor/stator mixers include SILVERSON in-line mixers, such as SILVERSON Model 450LS, manufactured by SILVERSON Machines, Inc.; or those commercially available from IKA-Works Inc., Wilmington, N.C. 28405, and from Charles Ross and Son Company, Hauppage, N.Y. 11788, including Models ME-410/420X, and 450X.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Continuous Loop Reactor

A continuous loop reactor was configured with a recycle loop wherein the reaction slurry could be circulated numerous times before it is discharged (see FIG. 1). The recycle loop comprised of sections of fixed pipe joined together by sections of flexible hose. The internal diameter of the piping/hose was approximately 1". On one side of the loop a pump was placed to circulate the reaction and on the opposite side a SILVERSON in-line mixer was installed to provide additional shear to the system and also to be used as an inlet port for introducing the acidulating agent. Between the pump and the mixer, a static mixer heat exchanger (KENICS Model 1-Pilot-HT-EX 32 available from Chemineer, Inc., Dayton, Ohio) was installed to provide a means to control the temperature during production of silica. The discharge pipe, located after the acidulating agent inlet port, allowed the product to discharge as a function of the rates at which silicate and acidulating agent are added. The discharge pipe can also be fitted with a back pressure valve that enables the reactor system to operate at temperatures greater than 100° C. The product discharge pipe can be oriented to collect product into a tank for additional modification (e.g., pH adjustment), or it can be discharged directly into a rotary or press type filter. Optionally, acid can also be added into the product discharge line to avoid post synthetic pH adjustments when product is being prepared at pH's greater than 7.0.

Example 2

Preparation of Silica Product

Silica product was prepared using the continuous loop reactor described in Example 1. Prior to the introduction of acidulating agent and alkali metal silicate into the continuous loop reactor, precipitated silica, sodium sulfate, sodium silicate, and water were first added and recirculated at 80 L/min. This is referred to herein as the liquid reaction medium, to which further acidulating agent and alkali metal silicate can be added, as discussed above. This initial step was performed to fill the recycle loop with the approximate contents and concentrations of a typical batch to thereby minimize the purging time before the desired silica product could be collected. It is believed that this step also minimizes gelation of the loop reactor contents. It should be noted, however, that acidulating agent and alkali metal silicate can be directly added to the loop reactor filled with only water without gelling or plugging the system. Thus, the liquid reaction medium can comprise water without seed silica prior to the introduction of the acidulating agent and the alkali metal silicate.

A solution of 1.5 kg of ZEODENT 103, 1.34 kg of sodium sulfate, 11.1 L of sodium silicate (2.65 MR, 13.3%) and 20 L of water was prepared. Approximately 15.5 L of this solution was then added to the recirculation loop of the loop reactor and it was heated to 68° C. The contents were recirculated at 80 L/min with a SILVERSON in-line mixer in the recirculating loop operating at 60 Hz (3485 RPM). Sodium silicate (2.65 MR, 13.3%) and sulfuric acid (11.4%) were added simultaneously to the loop at a silicate rate of 1.7 L/min and an acid rate sufficient to maintain a pH of 9.5. When necessary, the acid rate was adjusted accordingly to maintain the pH. Acid and silicate were added under these conditions for 40 minutes to purge unwanted silica out of the system before the desired silica product was collected. After 40 minutes had passed, the collection vessel was emptied and its contents discarded. Acid and silicate were continuously added while silica product was collected in a vessel with stirring at 40 RPM while maintaining the temperature at approximately 60° C. (unless otherwise specified, the collection temperature was the same as the reaction temperature). After the desired quantity of silica product was collected, addition of acid and silicate was stopped. The contents of the loop were allowed to circulate. The silica product in the collection vessel was adjusted to pH 5.0 with the manual addition of sulfuric acid and was then filtered and washed to a conductivity of approximately 1500 µS and subsequently dried.

Samples 2B to 2E were performed under the conditions shown in Table 3.

Samples 2F to 2S were performed according to Sample 2A with the exception that no pH adjustment was made prior to the washing/filtration step. Prior to drying, the pH of the product was adjusted to 5.5 with the manual addition of dilute sulfuric acid.

Sample 2J was performed according to Sample 2F with the exception that the pH was adjusted to 6.5 prior to drying.

Sample 2N was performed with the continuous loop reactor as described above with the exception that the stator was removed from the SILVERSON in line mixer.

residence time can then be multiplied by the number of passes/minute to get the mean number of passes.

$$\text{residence time (min)} = \frac{\text{system volume (L)}}{\text{combined raw material addition rate (L/min)}}$$

$$\text{number of passes/min} = \frac{\text{recirculation rate (L/min)}}{\text{system volume (L)}}$$

$$\text{residence time (min)} \times \frac{\text{number of passes}}{\text{(min)}} = \text{mean number of passes}$$

As the mean number of passes was increased, the sphericity and roundness characteristics of the particles improved.

Generally, the continuous loop reactor was easily able to maintain a given condition during the reaction. As discussed above, at a given silicate flow rate, the rate of acid was adjusted to achieve a desired pH. Once the acid rate had stabilized, continuous operation at a desired condition could be maintained. Adjustment of pH was achieved by modifying the rate of acid addition. Conditions ranging from pH 2.5 to 9.5 and temperatures ranging from 24 to 122° C. have been specifically tested and no blocking or gelling of the liquid reaction medium was observed.

TABLE 3

Summary of reaction conditions for Sample 2A to 2S.

| Sample | Sulfuric Acid (%) | Sodium Silicate (%) | Recirc. Rate (L/min) | Mean Number of Passes | Silverson RPM | Silicate Addition Rate (L/min) | pH | Rxn Temp (° C.) |
|---|---|---|---|---|---|---|---|---|
| 2A | 11.4 | 13.3 | 80 | 29 | 3485 | 1.7 | 9.5 | 68 |
| 2B | 11.4 | 13.3 | 43 | 16 | 3485 | 1.7 | 9.5 | 70 |
| 2K | 11.4 | 13.3 | 80 | 21 | 1743 | 2.6 | 9.5 | 58 |
| 2C | 11.4 | 13.3 | 80 | 21 | 3600 | 2.6 | 9.5 | 58 |
| 2D | 11.4 | 13.3 | 80 | 20 | 1743 | 2.6 | 9.5 | 93 |
| 2E | 11.4 | 13.3 | 80 | 20 | 3485 | 2.6 | 9.5 | 93 |
| 2F | 11.4 | 13.3 | 80 | 19 | 3485 | 2.6 | 7.2 | 43 |
| 2O | 5.7 | 6.7 | 80 | 26 | 3485 | 1.7 | 7.5 | 68 |
| 2G | 17.0 | 19.5 | 80 | 28 | 3485 | 1.7 | 7.5 | 68 |
| 2L | 11.4 | 13.3 | 72 | 18 | 1743 | 2.6 | 7.2 | 33 |
| 2M | 11.4 | 13.3 | 80 | 29 | 1743 | 1.7 | 7.3 | 94 |
| 2N | 11.4 | 13.3 | 80 | 28 | 1743 | 1.7 | 7.5 | 94 |
| 2J | 17.0 | 19.5 | 77 | 30 | 3485 | 1.7 | 7.5 | 122 |
| 2H | 11.4 | 13.3 | 80 | 28 | 1743 | 1.7 | 5.5 | 45 |
| 2I | 11.4 | 13.3 | 80 | 27 | 1743 | 1.7 | 2.5 | 44 |
| 2P | 17.0 | 19.5 | 20 | 19 | 3485 | 0.56 | 7.6 | 95 |
| 2Q | 17.0 | 19.5 | 40 | 37 | 3485 | 0.56 | 7.5 | 95 |
| 2R | 17.0 | 19.5 | 60 | 71 | 3485 | 0.56 | 8.2 | 95 |
| 2S | 11.4 | 13.3 | 80 | 29 | 3485 | 1.7 | 7.0 | 94 |

With reference to Table 3, the acidulating agent and the alkali metal silicate were added at a given rate and maintained at a given percentage relative to the liquid reaction medium. The acidulating agent was sulfuric acid, and the alkali metal silicate was sodium silicate.

The mean number of passes, or the approximate number of times a given particle will travel around the precipitation loop before it is discharged, can be calculated in the following manner. With reference to the equations shown below, the residence time of the silica product in the recirculation loop before discharge is calculated by dividing the system volume by the raw material rate (silicate addition rate+acid addition rate). The number of passes/minute can then be calculated by dividing the recirculation rate by the system volume. The Example 3

Silica particles prepared from Example 2

The silica products prepared in Example 2 were characterized. The reaction slurry particle size (particle size of particles in the recycle loop) under most reaction conditions tested was generally found to be about 4-8 µm, with most examples falling in the 4-6 µm range. The dry particle size and sphericity/roundness of the particles was directly related to the structure of the silica. As the structure was lowered, a higher percentage of unagglomerated particles with high sphericity and roundness with little change from the slurry particle size distribution resulted upon drying. As the structure was increased, the level of particle agglomeration increased, the sphericity and roundness of the particles decreased, and the average particle size increased upon drying.

Figure 2:
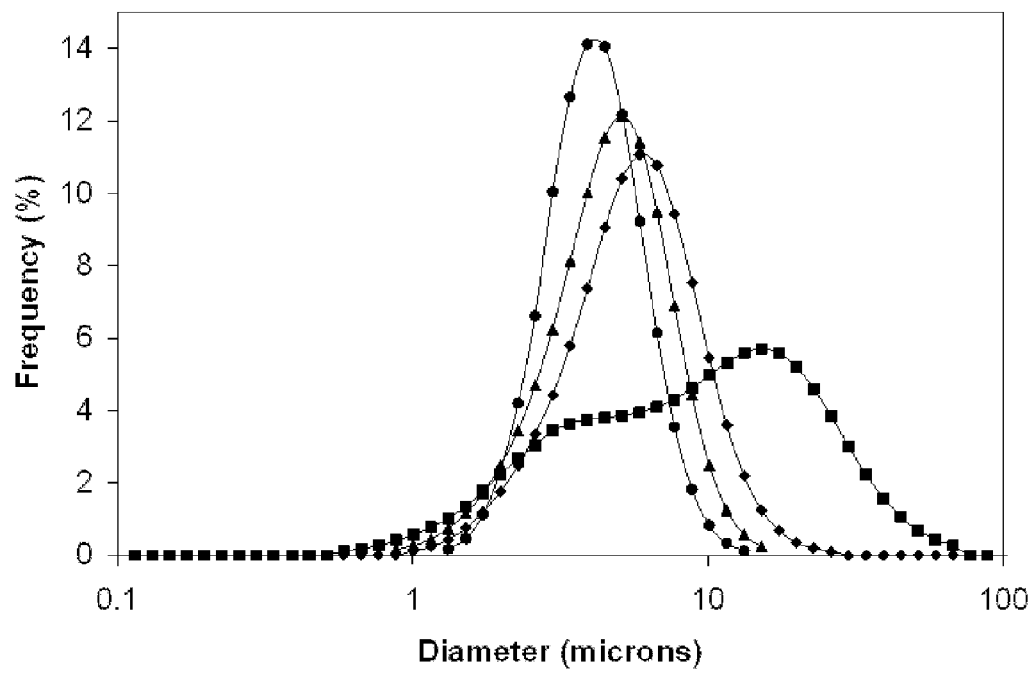
FIG. 2 is a plot showing Horiba particle size scans for Example 2E in slurry (circle), spray dried (diamond) and hammer milled (triangle). ZEODENT 103 silica is shown for comparison (square).

Higher structure samples can be reduced to their slurry particle sizes with gentle Raymond milling. More intense Raymond milling and also air milling did not substantially reduce the particle size much smaller than the slurry particle size. Milling of low structure products did not result in much of a change in particle size. The particle size distributions of the silica produced by the continuous process were Gaussian and typically less broad than precipitated silica prepared by conventional processes. Slurry, spray dried, Raymond milled and air milled particle sizes of the particles prepared with the continuous loop reactor are shown in Table 4. For the remaining examples, unmilled dried silica samples are designated with a "-1," Raymond milled samples with a "-2" and air milled samples with a "-3." Particle size distributions for silica product prepared by the continuous loop process and conventional processes are shown in FIG. 2.

TABLE 4

Slurry, spray dried and milled particle size of silica products prepared by continuous loop process.

| Sample | Slurry APS (Horiba median, μm) | Dry APS (Horiba median, μm) | Raymond milled APS (Horiba median, μm) | Air milled APS (Horiba median, μm) |
|---|---|---|---|---|
| 2A | 4.8 | 8.8 | — | — |
| 2B | 5.4 | 10.3 | 6.2 | 5.4 |
| 2C | 5.3 | 12.2 | 5.4 | — |
| 2D | 4.5 | 4.8 | — | 5.0 |
| 2E | 3.8 | 5.3 | — | 4.4 |
| 2F | 6.4 | 18.1 | 5.7 | 5.7 |
| 2G | 5.1 | 9.3 | 5.9 | 5.4 |
| 2H | — | 26.1 | 11.7 | — |
| 2I | — | 19.6 | 10.5 | — |
| 2J | 4.2 | 5.5 | — | 4.6 |
| 2K | 5.4 | 12.4 | — | — |
| 2L | 8.2 | 20.4 | — | — |
| 2M | 5.7 | 8.0 | — | — |
| 2N | 4.7 | 8.0 | — | — |
| 2O | 4.7 | 14.2 | — | — |
| 2P | — | 7.2 | — | — |
| 2Q | 5.0 | 6.3 | — | — |
| 2R | 4.3 | 5.4 | — | — |
| 2S | 4.6 | 7.5 | — | — |

The reaction conditions described above and listed in Table 3 allowed for the production of exemplary silica products with "low" to "medium high structures," with oil absorption values generally ranging from 32 to 171 cc/100 g. Moisture corrected water AbC values for the silica products produced ranged from 57 to 272 cc/100 g. CTAB surface areas ranged from 10 to 250 m$^2$/g. The BET surface areas, which ranged from 17 to 425, were higher than typical precipitated silica materials produced by the conventional batch processes. The brightness values for the silica products prepared by the continuous process were very good, which is likely attributable to their high sphericity and roundness. The silica products produced by the continuous process disclosed herein exhibited brightness values typically greater than 96, with the exception of those prepared at pH's less than 7. The physical properties of the silica products prepared by the disclosed process are shown in Table 5.

TABLE 5

Physical properties of continuous reactor samples.

| Sample | Moisture Corrected Water AbC (cc/100 g) | Oil Absorption (cc/100 g) | BET Surface Area (m$^2$/g) | CTAB Surface Area (m$^2$/g) | Na$_2$SO$_4$ (%) | H$_2$O (%) | Hg Intruded Volume (ml/g) | 5% pH | Technidyne Brightness |
|---|---|---|---|---|---|---|---|---|---|
| 2A-1 | 79 | 68 | 232 | 50 | 5.23 | 6.5 | 1.79 | 4.6 | 97.7 |
| 2B-1 | 114 | 88 | 207 | 80 | 0.74 | 7.1 | 1.81 | 8.5 | 98.6 |
| 2B-2 | 100 | 64 | 120 | 52 | 0.51 | 7.5 | 1.30 | 8.7 | 97.5 |
| 2B-3 | 101 | 74 | 120 | 66 | 0.51 | 8.0 | 0.82 | 8.7 | 97.8 |
| 2C-1 | 139 | 106 | 353 | 95 | 0.35 | 7.9 | 2.06 | 8.9 | 98.3 |
| 2C-2 | 109 | 83 | 178 | 98 | 0.35 | 7.6 | 0.74 | 9.0 | 96.4 |
| 2D-1 | 80 | 60 | 133 | 29 | 0.35 | 6.5 | 1.13 | 8.7 | 98.2 |
| 2D-3 | 75 | 60 | 55 | 28 | 0.35 | 8.1 | 1.09 | 8.9 | 98.3 |
| 2E-1 | 78 | 60 | 219 | 32 | 0.35 | 7.7 | 1.16 | 7.3 | 98.3 |
| 2E-3 | 70 | 58 | 149 | 28 | 0.35 | 8.1 | 0.99 | 7.7 | 98.1 |
| 2F-1 | 212 | 134 | 383 | 194 | 3.97 | 6.3 | 2.85 | 7.1 | 97.5 |
| 2F-2 | 150 | 125 | 376 | 185 | 3.66 | 6.6 | 2.37 | 7.4 | 96.8 |
| 2F-3 | 157 | 130 | 247 | 187 | 3.1 | 6.9 | 2.25 | 7.2 | 97.1 |
| 2G-1 | 87 | 54 | 157 | 48 | 2.71 | 5.0 | 1.36 | 7.3 | 98.8 |
| 2G-2 | 81 | 53 | 121 | 78 | 2.16 | 6.0 | 1.08 | 7.6 | 96.6 |
| 2G-3 | 79 | 67 | 162 | 68 | 2.32 | 5.8 | 1.10 | 7.5 | 98.1 |
| 2H-1 | 272 | 171 | 361 | 250 | 1.1 | 8.6 | 3.24 | 8.5 | 94.2 |
| 2H-2 | 203 | 158 | 310 | 246 | 0.7 | 8.3 | 2.65 | 8.5 | 93.2 |
| 2I-1 | 215 | 160 | 374 | 232 | 0.4 | 9.0 | 3.11 | 8.5 | 97.2 |
| 2I-2 | 192 | 140 | 413 | 219 | 0.4 | 8.9 | 3.31 | 8.5 | 96.8 |
| 2J-1 | 57 | 32 | 17 | 10 | 0.9 | 4.2 | 0.63 | 8.4 | 95.4 |
| 2K-1 | 140 | 101 | 279 | 98 | 0.35 | 8.7 | 2.15 | 8.7 | 98.7 |
| L2-1 | 204 | 148 | 425 | 217 | 2.9 | 7.4 | 2.72 | 7.3 | 96.8 |
| L2-2 | 158 | 125 | 138 | 210 | 2.6 | 7.2 | 1.30 | 7.4 | 96.7 |
| 2M-1 | 76 | 62 | 70 | 50 | 1.6 | 4.6 | 1.03 | 7.4 | 98.0 |
| 2M-2 | 79 | 59 | 77 | 54 | 1.6 | 7.2 | 1.10 | 7.4 | 96.8 |

TABLE 5-continued

Physical properties of continuous reactor samples.

| Sample | Moisture Corrected Water AbC (cc/100 g) | Oil Absorption (cc/100 g) | BET Surface Area (m²/g) | CTAB Surface Area (m²/g) | Na$_2$SO$_4$ (%) | H$_2$O (%) | Hg Intruded Volume (ml/g) | 5% pH | Technidyne Brightness |
|---|---|---|---|---|---|---|---|---|---|
| 2N-1 | 75 | 59 | 59 | 47 | 1.6 | 4.6 | 1.08 | 7.4 | 96.7 |
| 2N-2 | 66 | 51 | 61 | 49 | 1.6 | 4.0 | 0.75 | 7.3 | 97.0 |
| 2O-1 | 138 | 101 | 166 | 83 | 2.39 | 5.8 | 2.35 | 6.4 | 98.5 |
| 2P-1 | 67 | 56 | 49 | 29 | 2.0 | 6.5 | 0.88 | 7.4 | 97.8 |
| 2Q-1 | 61 | 51 | 24 | 16 | 1.5 | 5.5 | 0.71 | 8.0 | 97.6 |
| 2R-1 | 59 | 54 | 39 | 21 | 1.7 | 4.8 | 0.66 | 7.8 | 97.9 |
| 2S-1 | 82 | 61 | 95 | 38 | 1.92 | 5.0 | 1.22 | 7.6 | 97.8 |

Particle size distributions of the exemplary silica particle batches prepared using the continuous process disclosed herein were also evaluated. The results are shown in Table 6. Coefficient of uniformity (Cu) is defined as $D_{60}/D_{10}$. Coefficient of curvature (Cc) is defined as $(D_{30}/(D_{10} \times D_{60}))$. The peak symmetry is defined as $(D_{90}-D_{50})/(D_{50}-D_{10})$, wherein a peak symmetry value of 1.0 would represent a perfectly symmetrical distribution.

TABLE 6

Particle size distribution properties.

| Sample | Coefficient of Uniformity | Coefficient of Curvature | Peak Symmetry |
|---|---|---|---|
| 2B-2 | 2.47 | 0.23 | 1.48 |
| 2B-3 | 2.37 | 0.26 | 1.60 |
| 2C-2 | 2.33 | 0.26 | 1.60 |
| 2C-3 | 2.43 | 0.29 | 1.35 |
| 2E-2 | 2.22 | 0.30 | 1.43 |
| 2F-2 | 1.98 | 0.23 | 1.44 |
| 2F-3 | 2.20 | 0.24 | 1.44 |

Scanning electron micrographs of the silica products prepared by the continuous process disclosed herein exhibited a much more spherical and homogeneous distribution relative to conventional silica. The level of sphericity/roundness was generally greater with low structure products, since they did not agglomerate as readily upon drying. As the structure level increased, the degree of sphericity/roundness and homogeneity of the particles decreased. When comparing silica products prepared with the continuous loop process to those produced by traditional batch technology, the differences in sphericity and roundness can be clearly observed. Scanning electron micrographs of low, medium, and medium-high structure silica products produced by the continuous loop reactor and those prepared by traditional batch processes are shown in FIGS. 3-6.

Modification to the level of shear imparted into the system by the SILVERSON in line mixer was also studied. Adjustment of the power input from 30 to 60 hz and removal of the stator from the SILVERSON in line mixer did not substantially impact the quality of the sphericity and roundness of the particles produced. The mean number of passes, however, correlated with sphericity and roundness of the particles. Samples 2P, 2Q and 2R were performed under similar conditions with the exception that the recirculation rate (and mean number of passes) was varied. Sample 2R, with the highest mean number of passes (71), was found to have the highest quality sphericity and particle roundness compared to Samples 2P and 2Q.

Example 4

Silica Particles Prepared From Different Acidulating Agents (i) 4A.

A solution comprised of 1.5 kg of ZEODENT 103, 1.34 kg of sodium sulfate, 11.1 L of sodium silicate (2.65 MR, 13.3%) and 20 L of water was prepared. Approximately 15.5 L of this solution was then added to the recirculation loop of the loop reactor described in Example 1 and it was heated to 50° C. The contents were recirculated at 78 L/min with a SILVERSON in-line mixer in the recirculation loop operating at 60 Hz (3485 RPM). Sodium silicate (2.65 MR, 13.3%) and carbon dioxide (99.9%) were added simultaneously to the loop at a silicate rate of 0.5 L/min and a carbon dioxide rate sufficient to maintain a pH of 9.3 (the approximate flow rate was 47 L/min). When necessary, the carbon dioxide flow rate was adjusted accordingly to maintain the pH. Carbon dioxide and silicate were added under these conditions for 40 minutes to purge unwanted silica out of the system before the desired material was collected. After 40 minutes had passed, the collection vessel was emptied and its contents discarded. Carbon dioxide and silicate were continuously added while silica product was collected in a vessel with stirring at 40 RPM while maintaining the temperature at approximately 50° C. After the desired quantity of product was collected, addition of carbon dioxide and silicate was stopped. The contents of the loop were allowed to circulate. The silica product in the collection vessel was adjusted to pH 6.0 with the manual addition of sulfuric acid and was then filtered, washed to a conductivity of approximately 1500 µS, was dried and milled, if necessary.

(ii) 4B.

Example 4B was performed according to the method of Example 4A with the exception that the sodium silicate contained 10% by weight sodium sulfate, the pH was maintained at 8.5 with an approximate carbon dioxide flow rate of 64 L/min.

(iii) 4C.

A solution comprised of 1.5 kg of ZEODENT 103, 1.34 kg of sodium sulfate, 11.1 L of sodium silicate (2.65 MR, 13.3%) and 20 L of water was prepared. Approximately 15.5 L of this solution was then added to the recirculation loop of the loop reactor and it was heated to 43° C. The contents were recirculated at 80 L/min with a SILVERSON in-line mixer in the recirculation loop operating at 60 Hz (3485 RPM). Sodium silicate (2.65 MR, 13.3%) and sulfuric acid (11.4%) containing sodium sulfate at a concentration of 23 g/L were added simultaneously to the loop at a silicate rate of 2.55 L/min and an acid rate sufficient to maintain a pH of 7.5. When necessary, the acid rate was adjusted accordingly to maintain the pH. Acid (containing sodium sulfate) and silicate were added under these conditions for 40 minutes to purge unwanted silica out of the system before the desired material was collected. After 40 minutes had passed, the collection vessel was emptied and its contents discarded. Acid (containing sodium sulfate) and silicate were continuously added while silica product was collected in a vessel with stirring at 40 RPM while maintaining the temperature at approximately 45° C. After the desired quantity of product was collected, addition of acid and silicate was stopped. The contents of the loop were allowed to circulate. The silica product in the collection vessel was then filtered and washed to a conductivity of approximately 1500 µS. Prior to spray drying, the pH was adjusted to pH 6.0 with the manual addition of sulfuric acid.

(iv) 4D.

Example 4D was performed according to Example 4C with the exception that the silicate rate was 1.7 L/min, the pH was maintained at 7.1, the reaction temperature was 95° C. and the collection temperature was maintained at approximately 90° C.

(v) 4E.

Example 4E was performed according to Example 5D with the exception that the silicate concentration was 19.5%, 17% sulfuric acid containing aluminum sulfate at a concentration of 8.5 g/L, the reaction temperature was 40° C. and the pH was maintained at 7.5.

ated. Einlehner abrasion values for the exemplary silica particles produced by the disclosed continuous process were significantly lower than expected, ranging from 1.8 to 8.1 mg lost/100 k rev. With conventional precipitated silica products, as the structure decreases, the Einlehner values typically increase. With the disclosed continuous process silica products, this trend was not observed. Einlehner values were consistent with particle size. Perspex abrasion values of the exemplary silica products tested were also much lower than expected, ranging from 3.3 to 8.7.

Percent transmission (% T) values ranged from about 20 to 80% by the 4% in sorbitol test method. Refractive index (RI) values greater than 1.439 were observed for all samples prepared. The increase in RI values over typical precipitated silica products was likely due to lower reaction temperatures. Powder RDA values for four samples tested ranged from 105 to 221 as tested using the Hefferren method. This test was performed by the Indiana University School of Dentistry.

The continuous process was also found to be useful for preparing silica products that are compatible with cationic ingredients, such as cetylpyridinium chloride (CPC). CPC is a cationic anti-microbial agent that is used in mouthwash formulations to reduce plaque, tartar and gingivitis. Conventional silica materials are not typically compatible with CPC due to the strong interaction between the cationic moiety of the CPC molecule and the negatively charged silica surface. In order to improve the compatibility of silica with CPC, very

TABLE 7

Physical properties of silica samples prepared in Example 4.

| Ex | Water AbC (cc/100 g) | Oil Absorption (cc/100 g) | BET Surface Area (m$^2$/g) | CTAB Surface Area (m$^2$/g) | Na$_2$SO$_4$ (%) | H$_2$O (%) | Hg Intruded Volume (ml/g) | 5% pH | Median Particle Size (µm) | Technidyne Brightness |
|---|---|---|---|---|---|---|---|---|---|---|
| 4A-1 | 76 | 134 | 193 | 194 | 5.6 | 8.4 | 1.14 | 7.7 | 6.5 | 99.1 |
| 4B-1 | 77 | 128 | 16 | 19 | — | — | — | — | 6.4 | — |
| 4C-2 | 155 | 121 | 424 | 186 | 4.0 | 5.4 | 2.02 | 7.1 | 5.8 | 97.1 |
| 4D-1 | 81 | 60 | 94 | 45 | 2.0 | 4.9 | 0.78 | 7.6 | 7.6 | 97.4 |
| 4E-2 | 119 | 104 | 358 | 164 | 3.6 | 6.5 | 1.28 | 7.5 | 5.7 | 97.8 |

In addition to sulfuric acid, additives and other acidulating agents can be used in the continuous loop reactor to produce precipitated silica. Examples 4A and 4B used carbon dioxide in the place of sulfuric acid as the acidulating agent. This was accomplished by introducing the gas into the continuous loop reactor through the SILVERSON mixer. Slower silicate rates (0.5 L/min) were used in these examples in order to give the carbon dioxide that was introduced sufficient time to react and maintain the desired pH, since the flow of carbon dioxide was limited. Since the carbon dioxide produces a weak acid (carbonic acid), pH targets of greater than 8.5 were used. The silica products resulting from Example 4A had high sphericity and roundness, as observed by (SEM). Raymond or air milling was not needed to achieve median particles sizes in the 5 to 7 µm range. Example 4C, 4D and 4E utilized a mixture of aqueous sodium sulfate and sulfuric acid as the acidulating agent and the physical properties are shown in Table 7.

Example 5

Dentifrice Compositions

Dentifrice compositions comprising the disclosed silica particles were prepared. A number of important properties for silica products useful in dentifrice compositions were evalulow structure silica products can be prepared with reduced available surface area for CPC binding. The production of CPC compatible silica products by conventional batch techniques can be problematic, since increased batch times are typically needed to achieve the necessary structure, and low brightness values can result from the milling of such highly dense silica. The use of the disclosed continuous process allows for low structure silica products to be prepared at acceptable production rates and with very good brightness values since hammer or air milling is not needed to achieve the desired particle size range. A summary of the dental silica testing performed is shown in Table 8.

TABLE 8

Abrasion and optical data from silica products prepared by the continuous process.

| Sample | Einlehner (mg lost/100k rev) | Perspex Abrasion (gloss reduction) | Powder RDA | RI (at max % T) | % T (4% in sorbitol) |
|---|---|---|---|---|---|
| 2A-1 | 2.5 | 3.8 | 221 | 1.448 | 58.8 |
| 2B-1 | 2.9 | 4.5 | — | 1.444 | 56.4 |
| 2B-2 | 3.2 | — | 169 | 1.439 | 48.2 |
| 2B-3 | 4.5 | — | — | 1.439 | 46.0 |

TABLE 8-continued

Abrasion and optical data from silica products prepared by the continuous process.

| Sample | Einlehner (mg lost/100k rev) | Perspex Abrasion (gloss reduction) | Powder RDA | RI (at max % T) | % T (4% in sorbitol) |
|---|---|---|---|---|---|
| 2K-1 | 3.5 | 7.0 | — | 1.439 | 64.0 |
| 2C-1 | 5.2 | 5.2 | — | 1.439 | 64.4 |
| 2D-1 | 3.3 | 7.8 | — | 1.439 | 22.8 |
| 2D-3 | 5.4 | — | — | 1.435 | 24.4 |
| 2E-1 | 1.8 | 3.9 | 130 | 1.439 | 20.0 |
| 2E-3 | 3.0 | — | — | 1.435 | 26.0 |
| 2S-1 | 4.7 | 8.7 | — | 1.439 | 42.8 |
| 2F-1 | 6.0 | — | — | 1.453 | 70.3 |
| 2F-2 | 4.3 | — | 105 | 1.447 | 60.2 |
| 2F-3 | 4.1 | — | — | 1.447 | 55.8 |
| 4C-1 | 2.1 | — | — | 1.453 | 80.6 |
| 4C-2 | 3.6 | — | — | 1.453 | 72.3 |
| 4C-3 | 3.6 | — | — | 1.453 | 73.0 |
| 4C-1 | 4.2 | — | — | 1.444 | 46.2 |
| 2O-1 | 3.9 | — | — | 1.444 | 70.4 |
| 2G-1 | 1.8 | — | — | 1.439 | 56.1 |
| 2G-2 | 2.2 | — | — | 1.439 | 54.2 |
| 2G-3 | 3.8 | — | — | 1.439 | 54.5 |
| 4A-1 | 3.6 | — | — | 1.439 | 45.8 |
| 2L-1 | 2.3 | — | — | — | — |
| 2L-2 | 2.8 | — | — | — | — |
| 2M-1 | 5.8 | — | — | — | — |
| 2M-2 | 6.2 | — | — | — | — |
| 2N-1 | 7.5 | — | — | — | — |
| 2N-2 | 7.0 | — | — | — | — |
| 2J-1 | 7.9 | — | — | — | — |
| 2P-1 | 7.1 | — | — | — | — |
| 2Q-1 | 8.1 | — | — | — | — |
| 2R-1 | 5.6 | — | — | — | — |

Several samples with structures that spanned the structure range were selected for formulation into toothpaste for PCR, RDA and REA testing. Samples were formulated into dentifrice at 20% loading and also at lower loading levels in combination with traditional silica materials. The formulations are shown in Tables 9-12. Several of these samples and a range of others were placed into two different formulations for dentifrice stability evaluation.

TABLE 9

Toothpaste formulation.

| Example 5 | Batch Formulation Number | | | | | | | | |
|---|---|---|---|---|---|---|---|---|---|
| | A | B | C | D | E | F | G | H | I |
| Glycerin, 99.5% | 11.0 | 11.0 | 11.0 | 11.0 | 11.0 | 11.0 | 11.0 | 11.0 | 11.0 |
| Sorbitol, 70.0% | 40.0 | 40.0 | 40.0 | 40.0 | 40.0 | 40.0 | 40.0 | 40.0 | 40.0 |
| Deionized Water | 20.0 | 20.0 | 20.0 | 20.0 | 20.0 | 20.0 | 20.0 | 20.0 | 20.0 |
| CARBOWAX 600 | 3.0 | 3.0 | 3.0 | 3.0 | 3.0 | 3.0 | 3.0 | 3.0 | 3.0 |
| CEKOL 500T | 1.2 | 1.2 | 1.2 | 1.2 | 1.2 | 1.2 | 1.2 | 1.2 | 1.2 |
| Tetrasodium Pyrophosphate | 0.5 | 0.5 | 0.5 | 0.5 | 0.5 | 0.5 | 0.5 | 0.5 | 0.5 |
| Sodium Saccharin | 0.2 | 0.2 | 0.2 | 0.2 | 0.2 | 0.2 | 0.2 | 0.2 | 0.2 |
| Sodium Fluoride | 0.243 | 0.243 | 0.243 | 0.243 | 0.243 | 0.243 | 0.243 | 0.243 | 0.243 |
| Zeodent 165 | 1.5 | 1.5 | 1.5 | 1.5 | 1.5 | 1.5 | 1.5 | 1.5 | 1.5 |
| Zeodent 103 | 20.0 | — | 10.0 | — | — | — | — | — | — |
| Zeodent 113 | — | 20.0 | 10.0 | — | — | — | 10.0 | 10.0 | 10.0 |
| 2F-2 | — | — | — | 20.0 | — | — | 10.0 | — | — |
| 2B-2 | — | — | — | — | 20.0 | — | — | 10.0 | — |
| 2E-1 | — | — | — | — | — | 20.0 | — | — | 10.0 |
| Titanium Dioxide | 0.5 | 0.5 | 0.5 | 0.5 | 0.5 | 0.5 | 0.5 | 0.5 | 0.5 |
| Sodium Lauryl Sulfate | 1.2 | 1.2 | 1.2 | 1.2 | 1.2 | 1.2 | 1.2 | 1.2 | 1.2 |
| Flavor | 0.65 | 0.65 | 0.65 | 0.65 | 0.65 | 0.65 | 0.65 | 0.65 | 0.65 |
| Total | 100 | 100 | 100 | 100 | 100 | 100 | 100 | 100 | 100 |

TABLE 10

Toothpaste formulation.

| Example 5 | Batch Formulation Number | | | | | | | |
|---|---|---|---|---|---|---|---|---|
| | J | K | L | M | N | O | P | Q |
| Glycerin, 99.5% | 11.2 | 11.2 | 11.2 | 11.2 | 11.2 | 11.2 | 11.2 | 11.2 |
| Sorbitol, 70.0% | 36.4 | 36.4 | 36.4 | 36.4 | 36.4 | 36.4 | 36.4 | 36.4 |
| Deionized Water | 18.8 | 18.8 | 18.8 | 18.8 | 18.8 | 18.8 | 18.8 | 18.8 |
| CARBOWAX 600 | 3.0 | 3.0 | 3.0 | 3.0 | 3.0 | 3.0 | 3.0 | 3.0 |
| CEKOL 2000 | 0.3 | 0.3 | 0.3 | 0.3 | 0.3 | 0.3 | 0.3 | 0.3 |
| Tetrasodium Pyrophosphate | 0.5 | 0.5 | 0.5 | 0.5 | 0.5 | 0.5 | 0.5 | 0.5 |
| Sodium Saccharin | 0.2 | 0.2 | 0.2 | 0.2 | 0.2 | 0.2 | 0.2 | 0.2 |
| Sodium Fluoride | 0.243 | 0.243 | 0.243 | 0.243 | 0.243 | 0.243 | 0.243 | 0.243 |
| Zeodent 165 | 7.0 | 7.0 | 7.0 | 7.0 | 7.0 | 7.0 | 7.0 | 7.0 |
| Zeodent 103 | 20.0 | — | — | — | — | — | — | — |
| Zeodent 124 | — | 20.0 | — | — | — | — | — | — |
| Zeodent 113 | — | — | 20.0 | — | — | — | — | — |
| 2B-2 | — | — | — | 20.0 | — | — | — | — |
| 2E-1 | — | — | — | — | 20.0 | — | — | — |
| 2E-3 | — | — | — | — | — | 20.0 | — | — |
| 2G-1 | — | — | — | — | — | — | 20.0 | — |
| 2G-3 | — | — | — | — | — | — | — | 20.0 |
| Titanium Dioxide | 0.5 | 0.5 | 0.5 | 0.5 | 0.5 | 0.5 | 0.5 | 0.5 |
| Sodium Lauryl Sulfate | 1.2 | 1.2 | 1.2 | 1.2 | 1.2 | 1.2 | 1.2 | 1.2 |
| Flavor | 0.65 | 0.65 | 0.65 | 0.65 | 0.65 | 0.65 | 0.65 | 0.65 |
| Total | 100 | 100 | 100 | 100 | 100 | 100 | 100 | 100 |

TABLE 11

Toothpaste formulation.

| Example 5 | Batch Formulation Number | | | | | | |
|---|---|---|---|---|---|---|---|
| | R | S | T | U | V | W | X |
| Glycerin, 99.5% | 5.0 | 5.0 | 5.0 | 5.0 | 5.0 | 5.0 | 5.0 |
| Sorbitol, 70.0% | 57.36 | 57.36 | 57.36 | 57.36 | 57.36 | 57.36 | 57.36 |
| Deionized Water | 11.0 | 11.0 | 11.0 | 11.0 | 11.0 | 11.0 | 11.0 |
| Carbowax 600 | 3.0 | 3.0 | 3.0 | 3.0 | 3.0 | 3.0 | 3.0 |
| Cekol 2000 | 0.8 | 0.8 | 0.8 | 0.8 | 0.8 | 0.8 | 0.8 |
| Sodium Saccharin | 0.2 | 0.2 | 0.2 | 0.2 | 0.2 | 0.2 | 0.2 |
| Sodium Fluoride | 0.24 | 0.24 | 0.24 | 0.24 | 0.24 | 0.24 | 0.24 |
| Zeodent 113 | 20.0 | — | — | — | — | — | — |
| 2B-1 | — | 20.0 | — | — | — | — | — |
| 2B-2 | — | — | 20.0 | — | — | — | — |
| 2C-1 | — | — | — | 20.0 | — | — | — |
| 2C-2 | — | — | — | — | 20.0 | — | — |
| 2F-2 | — | — | — | — | — | 20.0 | — |
| 4C-2 | — | — | — | — | — | — | 20.0 |
| Color, Blue 1.0% solution | 0.2 | 0.2 | 0.2 | 0.2 | 0.2 | 0.2 | 0.2 |
| Sodium Lauryl Sulfate | 1.2 | 1.2 | 1.2 | 1.2 | 1.2 | 1.2 | 1.2 |
| Flavor | 1.0 | 1.0 | 1.0 | 1.0 | 1.0 | 1.0 | 1.0 |
| Total | 100 | 100 | 100 | 100 | 100 | 100 | 100 |

TABLE 12

Toothpaste Formulation.

| Example 5 | Batch Formulation Number | | | | | | |
|---|---|---|---|---|---|---|---|
| | Y | Z | AA | AB | AC | AD | AE |
| Glycerin, 99.5% | 11.0 | 11.0 | 11.0 | 11.0 | 11.0 | 11.0 | 11.0 |
| Sorbitol, 70.0% | 40.0 | 40.0 | 40.0 | 40.0 | 40.0 | 40.0 | 40.0 |
| Deionized Water | 20.0 | 20.0 | 20.0 | 20.0 | 20.0 | 20.0 | 20.0 |
| Carbowax 600 | 3.0 | 3.0 | 3.0 | 3.0 | 3.0 | 3.0 | 3.0 |
| Cekol 500T | 1.2 | 1.2 | 1.2 | 1.2 | 1.2 | 1.2 | 1.2 |

TABLE 12-continued

Toothpaste Formulation.

| Example 5 | Batch Formulation Number | | | | | | |
|---|---|---|---|---|---|---|---|
| | Y | Z | AA | AB | AC | AD | AE |
| Tetrasodium Pyrophosphate | 0.5 | 0.5 | 0.5 | 0.5 | 0.5 | 0.5 | 0.5 |
| Sodium Saccharin | 0.2 | 0.2 | 0.2 | 0.2 | 0.2 | 0.2 | 0.2 |
| Sodium Fluoride | 0.243 | 0.243 | 0.243 | 0.243 | 0.243 | 0.243 | 0.243 |
| Zeodent 165 | 1.5 | 1.5 | 1.5 | 1.5 | 1.5 | 1.5 | 1.5 |
| Zeodent 103 | 20.0 | — | — | — | — | — | — |
| Zeodent 113 | — | — | — | 10.0 | 15.0 | — | — |
| 2G-2 | — | 20.0 | — | — | — | — | — |
| 2H-2 | — | — | — | — | — | 20.0 | 15.0 |
| 2J-1 | — | — | 20.0 | 10.0 | 5.0 | — | — |
| Titanium Dioxide | 0.5 | 0.5 | 0.5 | 0.5 | 0.5 | 0.5 | 0.5 |
| Sodium Lauryl Sulfate | 1.2 | 1.2 | 1.2 | 1.2 | 1.2 | 1.2 | 1.2 |
| Flavor | 0.65 | 0.65 | 0.65 | 0.65 | 0.65 | 0.65 | 0.65 |
| Total | 100 | 100 | 100 | 100 | 100 | 100 | 100 |

Properties of the toothpaste formulations listed Tables 9-12 are shown in Table 13. The toothpaste samples prepared were found to have acceptable aesthetic properties after 6 weeks of ageing at 25° C. The fluoride availability values were all greater than 85% after the same period of time. Viscosity build of the silica products produced by the continuous silica process was similar to a low structure silica for all samples with the exception of Examples 5W and 5X, which were more efficient at building viscosity than ZEODENT 113.

PCR, RDA and REA values were measured for a range of silica products. The PCR values ranged from 83 (Example 5AE) to 107 (Example 5AA) for the samples tested. When formulated at loading levels of 10 to 15%, PCR values were generally in the 90-100 range. Dentifrice RDA values ranged from 94 to 315, depending upon the structure and the loading level of the silica tested. Example 5AA, a 20% loading of the silica prepared in 2J, had the highest RDA value of 315. This was the lowest structure silica product produced and thus was the most abrasive. When formulated in combination with traditional silica materials, such as ZEODENT 113, at loading levels in the 5 to 10% loading range, cleaning improvements over ZEODENT 113 alone were observed. Several silica products produced by the continuous loop reactor at higher structure levels were also tested and found to have PCR values similar to a traditional high cleaning silica materials (Examples 5X and 5W) and were found to build viscosity more efficiently than dentifrice containing 20% loading of ZEODENT 113 (Example 5R). The cleaning properties of higher structure silica products prepared with the continuous loop reactor exhibited much higher PCR and RDA values than traditional medium to high structure silica materials. The silica products in Examples 5X and 5W exhibit a bifunctional nature, in that they provide very good cleaning while providing a sufficient viscosity build.

REA values for the low to medium structure silica products produced by the continuous loop reactor were lower or equal to those of ZEODENT 113, indicating the spherical nature of these materials may be less abrasive to enamel than traditional high cleaning silica materials, such as ZEODENT 103. Dentifrice testing data is summarized in Table 13.

TABLE 13

Dentifrice data for formulations shown in Tables 7-10.

| Example | 25% pH | 1 Week Viscosity (cps) | 3 Week Viscosity (cps) | 6 Week Viscosity (cps) | 6 Week Fluoride Availability At 25° C. (%) | PCR | RDA | REA |
|---|---|---|---|---|---|---|---|---|
| 5A | — | — | — | — | — | 98 | 156 | 7.2 |
| 5B | — | — | — | — | — | — | — | 5.8 |
| 5C | — | — | — | — | — | 94 | 129 | — |
| 5D | — | — | — | — | — | 96 | 122 | 4.6 |
| 5E | — | — | — | — | — | 92 | 133 | 4.7 |
| 5F | — | — | — | — | — | 99 | 174 | 5.8 |
| 5G | — | — | — | — | — | 88 | 113 | — |
| 5H | — | — | — | — | — | 92 | 125 | — |
| 5I | — | — | — | — | — | 100 | 161 | — |
| 5J | 7.5 | 319,000 | 370,000 | 354,000 | 93 | — | — | — |
| 5K | 7.4 | 505,000 | 601,000 | 631,000 | 92 | — | — | — |
| 5L | 7.2 | 997,000 | 895,000 | 1,036,000 | 91 | — | — | — |
| 5M | 8.0 | 493,000 | 531,000 | 591,000 | 90 | — | — | — |
| 5N | 7.3 | 241,000 | 262,000 | 300,000 | 88 | — | — | — |
| 5O | 7.3 | 275,000 | 293,000 | 319,000 | 86 | — | — | — |
| 5P | 7.6 | 317,000 | 379,000 | 380,000 | 88 | — | — | — |
| 5Q | 7.4 | 299,000 | 319,000 | 362,000 | 89 | — | — | — |
| 5R | 6.6 | 222,000 | 257,000 | 260,000 | 98 | — | — | — |
| 5S | 8.2 | 144,000 | 156,000 | 170,000 | 100 | — | — | — |
| 5T | 8.1 | 143,000 | 155,000 | 171,000 | 100 | — | — | — |
| 5U | 8.0 | 195,000 | 206,000 | 242,000 | 97 | — | — | — |
| 5V | 8.0 | 175,000 | 187,000 | 196,000 | 95 | — | — | — |

TABLE 13-continued

Dentifrice data for formulations shown in Tables 7-10.

| Example | 25% pH | 1 Week Viscosity (cps) | 3 Week Viscosity (cps) | 6 Week Viscosity (cps) | 6 Week Fluoride Availability At 25° C. (%) | PCR | RDA | REA |
|---|---|---|---|---|---|---|---|---|
| 5W | 7.6 | 288,000 | 317,000 | 328,000 | 93 | — | — | — |
| 5X | 7.4 | 353,000 | 384,000 | 370,000 | 92 | — | — | — |
| 5Y | — | — | — | — | — | 100 | 228 | — |
| 5Z | — | — | — | — | — | 104 | 261 | — |
| 5AA | — | — | — | — | — | 107 | 315 | — |
| 5AB | — | — | — | — | — | 104 | 290 | — |
| 5AC | — | — | — | — | — | 103 | 231 | — |
| 5AD | — | — | — | — | — | 87 | 111 | — |
| 5AE | — | — | — | — | — | 83 | 94 | — |

Example 6

Preparation of Sodium Alumino Silicate and Sodium Magnesium Alumino Silicate (i) 6A A solution of 1.5 kg of ZEODENT 103, 1.34 kg of sodium sulfate, 11.1 L of sodium silicate (3.32 MR, 20.0%) and 20 L of water was prepared. Approximately 15.5 L of this solution was then added to the recirculation loop of the loop reactor described in Example 1 and it was heated to 60° C. The contents were recirculated at 80 L/min with a SILVERSON in-line mixer in the recirculating loop operating at 60 Hz (3485 RPM). Sodium silicate (3.32 MR, 20.0%) and aqueous aluminum sulfate (11.4%) were added simultaneously to the loop at a silicate rate of 1.7 L/min and an aluminum sulfate rate sufficient to maintain a pH of 8.5. When necessary, the acid rate was adjusted accordingly to maintain the pH. Acid and silicate were added under these conditions for 40 minutes to purge unwanted silica out of the system before the desired material was collected. After 40 minutes had passed, the collection vessel was emptied and its contents discarded. Acid and aluminum sulfate were continuously added while silicate product was collected in a vessel with stirring at 40 RPM while maintaining the temperature at approximately 60° C. After the desired quantity of product was collected, addition of aluminum sulfate and silicate was stopped. The contents of the loop were allowed to circulate. The silicate product in the collection vessel was then filtered, washed to a conductivity of approximately 1500 μS and was dried.

(ii) 6B.

Example 6B was performed according to Example 6A with the exception that recirculation rate was 77 L/min and the reaction temperature was 36° C. and the collection vessel temperature was held at ambient temperature. The sample was Raymond milled after drying.

(iii) 6C.

Example 6C was performed according to Example 6B with the exception that the static mixer heat exchanger was removed from the apparatus and the reaction temperature was 32° C.

(iv) 6D.

Example 6D was performed according to Example 6C with the exception that the aqueous aluminum sulfate concentration was 14.5%, a silicate rate of 3.4 L/min and a reaction temperature of 24° C.

(v) 6E.

The static mixer heat exchanger was removed from the loop reactor. A solution comprised of 1.5 kg of ZEODENT 103, 1.34 kg of sodium sulfate, 11.1 L of sodium silicate (3.32 MR, 20.0%) and 20 L of water was prepared. Approximately 15.5 L of this solution was then added to the recirculation loop of the loop reactor and it was heated to 39° C. The contents were recirculated at 110 L/min with a SILVERS ON in-line mixer in the recirculation loop operating at 60 Hz (3485 RPM). Sodium silicate (3.32 MR, 20.0%) containing magnesium hydroxide at 4.5 g/L and aqueous aluminum sulfate (34.0%) were added simultaneously to the loop at a silicate rate of 2.5 L/min and an aqueous aluminum sulfate rate sufficient to maintain a pH of 8.8. When necessary, the aqueous aluminum sulfate rate was adjusted accordingly to maintain the pH. Aqueous aluminum sulfate and silicate containing magnesium hydroxide were added under these conditions for 25 minutes to purge unwanted silica out of the system before the desired material was collected. After 25 minutes had passed, the collection vessel was emptied and its contents discarded. Aqueous aluminum sulfate and silicate containing magnesium hydroxide were continuously added while silicate product was collected in a vessel with stirring at 40 RPM while maintaining the temperature at approximately 39° C. After the desired quantity of product was collected, addition of aqueous aluminum sulfate and silicate containing magnesium hydroxide was stopped. The contents of the loop were allowed to circulate. The silicate product in the collection vessel was then filtered, washed to a conductivity of approximately 1500 μS and was dried.

TABLE 14

Physical properties for silica products prepared in Example 6.

| Ex | Water AbC (cc/100 g) | Oil Absorption (cc/100 g) | BET Surface Area (m²/g) | CTAB Surface Area (m²/g) | $Na_2SO_4$ (%) | $H_2O$ (%) | Hg Intruded Volume (ml/g) | 5% pH | Median Particle Size (μm) | Technidyne Brightness |
|---|---|---|---|---|---|---|---|---|---|---|
| 6A-1 | 79 | 68 | 232 | 50 | 5.2 | 6.5 | 1.30 | 4.7 | 8.8 | 97.7 |
| 6B-1 | 91 | 68 | 198 | 109 | 0.1 | 6.5 | 0.53 | 8.4 | 11.7 | 99.2 |
| 6B-2 | 79 | 68 | 180 | 80 | 0.1 | 7.3 | 0.80 | 8.4 | 5.7 | 98.0 |
| 6C-1 | 91 | 78 | 222 | 93 | 0.1 | 7.7 | 1.16 | 7.9 | 9.9 | 99.3 |

TABLE 14-continued

Physical properties for silica products prepared in Example 6.

| Ex | Water AbC (cc/100 g) | Oil Absorption (cc/100 g) | BET Surface Area (m²/g) | CTAB Surface Area (m²/g) | $Na_2SO_4$ (%) | $H_2O$ (%) | Hg Intruded Volume (ml/g) | 5% pH | Median Particle Size (μm) | Technidyne Brightness |
|---|---|---|---|---|---|---|---|---|---|---|
| 6C-2 | 83 | 60 | 178 | 86 | 0.1 | 7.4 | 1.67 | 8.0 | 6.6 | 98.9 |
| 6D-2 | 137 | 122 | 272 | 160 | 1.1 | 8.4 | 1.02 | 9.6 | 6.4 | 97.6 |
| 6E-1 | 115 | 68 | 369 | 153 | 0.3 | 10.8 | 1.53 | 10.3 | 10.7 | 98.4 |
| 6E-2 | 119 | 68 | 213 | 174 | 0.3 | 10.2 | 0.96 | 10.2 | 6.2 | 97.8 |

Examples 6A, 6B, 6C and 6D describe the preparation of sodium alumino silicates in the continuous loop reactor by the neutralization of sodium silicate with aqueous aluminum sulfate. The aqueous aluminum sulfate was introduced into the loop reactor through the SILVERSON in line mixer. Modification of the number of passes was used to produce a range of products with oil absorption values ranging from approximately 60 to 122 cc/100 g. Example 6E describes the preparation of sodium magnesium alumino silicate by the neutralization of sodium silicate/magnesium hydroxide with aqueous aluminum sulfate. Properties of these silica products are listed in Table 14. The materials produced in these examples had high sphericity values and were well rounded in nature. Materials such as these may have applicability in paint and coatings and paper applications.

Various modifications and variations can be made to the compounds, composites, kits, articles, devices, compositions, and methods described herein. Other aspects of the compounds, composites, kits, articles, devices, compositions, and methods described herein will be apparent from consideration of the specification and practice of the compounds, composites, kits, articles, devices, compositions, and methods disclosed herein. It is intended that the specification and examples be considered as exemplary.

What is claimed is:

1. Silica particles having an oil absorption value of up to 100 cc/100 g; wherein at least 80% of the silica particles are rounded to well rounded; and wherein the silica particles have a sphericity ($S_{80}$) factor of greater than 0.9 and a Brass Einlehner Abrasion value of less than 8.0 mg lost/100,000 revolutions.

2. The silica particles of claim 1, wherein the silica particles have a median particle size of from 3 to 15 μm.

3. The silica particles of claim 1, wherein the silica particles have a median particle size of from 3 to 10 μm.

4. The silica particles of claim 1, wherein the silica particles have an oil absorption value of from 30 to 80 cc/100 g.

5. The silica particles of claim 1, wherein the silica particle have a BET surface area of from 50 to 350 m²/g.

6. A dentifrice composition comprising silica particles in an amount ranging from 5 to 50% by weight of the composition; wherein the silica particles have an oil absorption value of up to 100 cc/100 g, a sphericity ($S_{80}$) factor of greater than 0.9, and a Brass Einlehner Abrasion value of less than 8.0 mg lost/100,000 revolutions; wherein at least 80% of the silica particles are rounded to well rounded.

7. The dentifrice composition of claim 6, wherein the composition comprises one or more of a humectant, a solvent, a binder, a therapeutic agent, a chelating agent, a thickener other than the silica particles, a surfactant, an abrasive other than the silica particles, a sweetening agent, a colorant, a flavoring agent, or a preservative.

8. The dentifrice composition of claim 6, wherein the silica particles have a median particle size of from 3 to 15 μm.

9. The dentifrice composition of claim 6, wherein the silica particles have a median particle size of from 3 to 10 μm.

10. The dentifrice composition of claim 6, wherein the silica particles have an oil absorption value of from 30 to 80 cc/100 g.

11. The dentifrice composition of claim 6, wherein the silica particles have a BET surface area of from 50 to 350 m²/g.

12. The dentifrice composition of claim 6, wherein the composition has a Radioactive Dentin Abrasion (RDA) value of at least 100.

13. The dentifrice composition of claim 6, wherein the composition has a Pellicle Cleaning Ratio (PCR) value of at least 85.

* * * * *